US010029962B2

(12) United States Patent
Ondrus et al.

(10) Patent No.: US 10,029,962 B2
(45) Date of Patent: Jul. 24, 2018

(54) PROCESS FOR PRODUCING $C_3$ CHLORINATED ALKANE AND ALKENE COMPOUNDS

(71) Applicant: SPOLEK PRO CHEMICKOU A HUTNI VYROBU A.S., Usti nad Labem (CZ)

(72) Inventors: Zdenek Ondrus, Vrbice (CZ); Pavel Kubicek, Decin (CZ); Petr Sladek, Usti nad Labem-Strekov (CZ)

(73) Assignee: SPOLEK PRO CHEMICKOU A HUTNI VYROBU A.S., Usti nad Labem (CZ)

( * ) Notice: Subject to any disclaimer, the term of this patent is extended or adjusted under 35 U.S.C. 154(b) by 0 days.

(21) Appl. No.: 15/237,942

(22) Filed: Aug. 16, 2016

(65) Prior Publication Data

US 2017/0050904 A1 Feb. 23, 2017

(30) Foreign Application Priority Data

Aug. 19, 2015 (CZ) ...................... 2015-558
Dec. 3, 2015 (CZ) ...................... 2015-858

(51) Int. Cl.
*C07C 17/10* (2006.01)
*C07C 17/383* (2006.01)
*C07C 17/25* (2006.01)

(52) U.S. Cl.
CPC ............ *C07C 17/383* (2013.01); *C07C 17/10* (2013.01); *C07C 17/25* (2013.01); *Y02P 20/582* (2015.11)

(58) Field of Classification Search
CPC ..................................... C07C 17/10
See application file for complete search history.

(56) References Cited

U.S. PATENT DOCUMENTS 3,823,195 A 7/1974 Smith et al.
3,926,758 A 12/1975 Smith
(Continued)

FOREIGN PATENT DOCUMENTS

WO WO-98/05614 2/1998
WO WO-2012/098420 7/2012
(Continued)

*Primary Examiner* — Medhanit W Bahta
(74) *Attorney, Agent, or Firm* — Pearl Cohen Zedek Latzer Baratz LLP

(57) ABSTRACT

A process for producing a reaction mixture comprising a plurality of $C_3$ chlorinated alkane isomers comprising chlorinating a $C_3$ chlorinated alkane starting material in a chlorination zone to produce the plurality of $C_3$ chlorinated alkane isomers, the plurality of $C_3$ chlorinated alkane isomers each having at least one more chlorine atom than the $C_3$ chlorinated alkane starting material, wherein the concentration of the $C_3$ chlorinated alkane starting material is controlled such that conversion of the $C_3$ chlorinated alkane starting material to the plurality of $C_3$ chlorinated alkane isomers, represented by the molar ratio of the $C_3$ chlorinated alkane starting material:$C_3$ chlorinated alkane isomers in the reaction mixture present in the chlorination zone, does not exceed about 40:60.

6 Claims, 3 Drawing Sheets

(56) References Cited

U.S. PATENT DOCUMENTS

| | | | |
|---|---|---|---|
| 5,705,779 A * | 1/1998 | Demmin | C07C 17/10 |
| | | | 204/157.6 |
| 8,252,964 B2 | 8/2012 | Devic et al. | |
| 8,907,147 B2 | 12/2014 | Wang et al. | |
| 2010/0331583 A1 | 12/2010 | Johnson et al. | |
| 2012/0157723 A1 | 6/2012 | Fukuju et al. | |
| 2013/0165705 A1 * | 6/2013 | Hosaka | C07C 17/06 |
| | | | 570/227 |
| 2014/0171698 A1 | 6/2014 | Elsheikh et al. | |
| 2014/0235903 A1 | 8/2014 | Wang et al. | |
| 2016/0207855 A1 | 7/2016 | Wedlinger et al. | |

FOREIGN PATENT DOCUMENTS

| | | |
|---|---|---|
| WO | WO-2013/015068 | 1/2013 |
| WO | WO 2013/022676 | 2/2013 |
| WO | WO 2013/022677 | 2/2013 |
| WO | WO-2013/055894 | 4/2013 |
| WO | WO-2013/074324 | 5/2013 |
| WO | WO-2013/086262 | 6/2013 |
| WO | WO 2013/088195 | 6/2013 |
| WO | WO-2013/119919 | 8/2013 |
| WO | WO-2013/184865 | 12/2013 |
| WO | WO-2014/116562 | 7/2014 |
| WO | WO-2014/120865 | 8/2014 |
| WO | WO-2014/130445 | 8/2014 |
| WO | WO-2016/058566 | 4/2016 |
| WO | WO-2016/058567 | 4/2016 |
| WO | WO-2016/058568 | 4/2016 |

\* cited by examiner

PROCESS FOR PRODUCING C₃ CHLORINATED ALKANE AND ALKENE COMPOUNDS

This application claims the benefit of Czech Republic Patent Application PV 2015-558, filed Aug. 19, 2015 and Czech Republic Patent Application PV 2015-858, filed Dec. 3, 2015, both of which are incorporated by reference.

The present invention relates to processes for producing very high purity $C_3$ chlorinated alkane and alkene compounds which may be used, for example, as feedstocks for the production of new generation fluorochemicals. The invention also relates to compositions obtained from such processes and the use of those compositions in the preparation of fluorochemicals.

Haloalkanes find utility in a range of applications. For example, halocarbons are used extensively as refrigerants, blowing agents and foaming agents. Throughout the second half of the twentieth century, the use of chlorofluoroalkanes increased exponentially until the 1980's, when concerns were raised about their environmental impact, specifically regarding depletion of the ozone layer.

Subsequently, fluorinated hydrocarbons such as perfluorocarbons and hydrofluorocarbons have been used in place of chlorofluoroalkanes, although more recently, environmental concerns about the use of that class of compounds have been raised and legislation has been enacted in the EU and elsewhere to reduce their use.

New classes of environmentally friendly halocarbons are emerging and have been investigated, for example, those having low ozone depletion/global warming potential, and already in some cases, are embraced in a number of applications, especially as refrigerants in the automotive and domestic fields. Examples of such compounds include 2-chloro-3,3,3-trifluoropropene (HFO-1233xf), 1,3,3,3-tetrafluoropropene (HFO-1234ze), 3,3,3-trifluoropropene (HFO-1243zf), 2,3,3,3-tetrafluropropene (HFO-1234yf), 1,2,3,3,3-pentafluoropropene (HFO-1225ye), 1-chloro-3,3,3-trifluoropropene (HFO-1233zd), 3,3,4,4,4-pentafluorobutene (HFO-1345zf), 1,1,1,4,4,4-hexafluorobutene (HFO-1336mzz), 3,3,4,4,5,5,5-heptafluoropentene (HFO-1447fz), 2,4,4,4-tetrafluorobut-1-ene (HFO-1354mfy) and 1,1,1,4,4,5,5,5-octafluoropentene (HFO-1438mzz). As those skilled in the art will recognize that 'HFO' is an abbreviation for hydrofluoroolefin, i.e. an unsaturated compound comprising carbon, hydrogen and fluorine atoms.

Unless otherwise stated, structures depicted herein are also meant to include all isomeric forms of the structure, for example (Z) and (E) (or cis or trans) double bond isomers, and (Z) and (E) (or cis or trans) conformational isomers.

While these compounds are, relatively speaking, chemically non-complex, their synthesis on an industrial scale to the required levels of purity is challenging. Many synthetic routes proposed for such compounds increasingly use, as starting materials or intermediates, chlorinated alkanes or alkenes. Examples of such processes are disclosed in WO2012/098420, WO2013/015068 and US2014/171698. The conversion of the chlorinated alkane or alkene starting materials to the fluorinated target compounds is usually achieved using hydrogen fluoride and optionally transition metal catalysts, for example chromium-based catalysts.

An example of an optionally non-catalytic process for preparing fluoroalkenes is disclosed in WO2013/074324.

Examples of processes known to those skilled in the art for preparing several of the HFO compounds listed above, starting from a $C_3$ chlorinated alkane/alkene feedstock include:

1,1,1,2,3-pentachloropropane (HCC-240db) to 2-chloro-3,3,3-trifluoro-1-propene (HFCO-1233xf);
1,1,2,2,3-pentachloropropane (HCC-240aa) to 2-chloro-3,3,3-trifluoro-1-propene (HFCO-1233xf);
1,1,1,2,3-pentachloropropane (HCC-240db) to 2,3,3,3-tetrafluoro-1-propene (HFO-1234yf);
1,1,2,2,3-pentachloropropane (HCC-240aa) to 2,3,3,3-tetrafluoro-1-propene (HFO-1234yf);
1,1,2,3-tetrachloro-1-propene (HCO-1230xa) to 2-chloro-3,3,3-trifluoro-1-propene (HFCO-1233xf);
1,1,2,3-tetrachloro-1-propene (HCO-1230xa) to 2,3,3,3-tetrafluoro-1-propene (HFO-1234yf)
1,1,3,3-tetrachloro-1-propene (HCO-1230za) to 1,1,1-trifluoro-3-chloro-1-propene (HFCO-1233zd), 1,1,1,3-tetrafluoro-1-propene (HFO-1234ze), 1,1,1,3,3-pentafluoropropane (HFC-245fa) and mixtures thereof
2,3,3,3-tetrachloro-1-propene (HCO-1230xf) to 2-chloro-3,3,3-trifluoro-1-propene (HFCO-1233xf).
2,3,3,3-tetrachloro-1-propene (HCO-1230xf) to 2,3,3,3-tetrafluoro-1-propene (HFO-1234yf);
2-chloro-3,3,3-trifluoro-1-propene (HFCO-1233xf) to 2,3,3,3-tetrafluoro-1-propene (HFO-1234yf);
2,3-dichloro-1,1,1-trifluoropropane (HCFC-243db) to 2-chloro-3,3,3-trifluoro-1-propene (HFCO-1233xf);
2,3-dichloro-1,1,1-trifluoropropane (HCFC-243db) to 2,3,3,3-tetrafluoro-1-propene (HFO-1234yf).

The issue of the formation of impurities during hydrofluorination reactions is known and is of concern especially given that certain impurities can impede continuous hydrofluorination on an industrial scale and/or result in the formation of unwanted fluorinated compounds which are difficult to remove from the final target HFO compounds. Those unwanted HFO compounds not only render the target HFO compound/s impure, but also may have toxic effects and/or interfere with the desired operation of the target HFO in its intended application, for example as blowing agents or heat transfer fluids, e.g. refrigerants.

Attempts to prevent or retard the formation of unwanted impurities in HFO production are disclosed in the prior art. For example, US2010/331583 and WO2013/119919 describe the need for purity in the part fluorinated feedstock (as well as approaches for improving purity). Additionally, U.S. Pat. No. 8,252,964 describes use of molecular sieves to remove impurities from HFO compounds. WO2013/184865 advocates the use of further reactions to separate out difficult to remove impurities from HFO compounds of interest. US2014/235903 addresses the problem of reactor impurities.

The purity of the chlorinated starting materials will have a substantial effect on the success and viability of the processes (especially continuous processes) for preparing the desirable fluorinated products. The presence of certain impurities will result in side reactions, minimising the yield of the target compound. Impurities in the chlorinated feedstock will also be transformed into fluorinated impurities in the HFO compound of interest. Removal of these impurities through the use of distillation steps is also challenging and/or inefficient. Additionally, the presence of certain impurities will compromise catalyst life, by, for example, acting as catalyst poisons.

A variety of impurities can exist in the chlorinated feedstock, e.g. oxygenated compounds, chlorinated alkanes other than the compound of interest, under chlorinated compounds (i.e. compounds comprising fewer chlorine atoms than the compound of interest), over chlorinated compounds (i.e. compounds comprising more chlorine atoms than the compound of interest), isomers of the target compound, and/or residues of any catalysts used.

It has been recognised that when the chlorinated feedstock is itself obtained from a multi-step process, especially if such steps are linked and run continuously to achieve industrially acceptable product volumes, then the need to prevent cumulative side reactions from generating unacceptable impurities at each process step is very important. This is important for $C_3$ chlorinated compounds, as conventional processes for producing such compounds are often affected by the formation of a range of side products. Accordingly, it is generally desirable to streamline processes for producing such compounds so that fewer steps are involved. Examples of attempts to improve the efficiency of processes for preparing $C_3$ chlorinated compounds are disclosed in U.S. Pat. No. 8,907,147, which describes the use of reactive distillation processes which combine two reactions in one reactor system and WO2014/116562, which describes the direct production of 240db, by chlorination of 250fb using antimony based catalysts.

Accordingly, there is a need for $C_3$ chlorinated alkanes and alkenes having controlled and acceptable impurity profiles for use in the synthesis of the fluorinated compounds mentioned above. Several processes for producing purified chlorinated compounds have been proposed in the art.

For example, WO2013/086262 discloses a process for preparing 1,1,2,2,3-pentachloropropane from methylacetylene gas. As can be seen from the examples in that application, the bench scale syntheses disclosed therein resulted in a product having around 98.5% purity, despite being subjected to post-synthetic purification process, specifically distillation.

In WO2014/130445, a conventional process is discussed on page 2 of that publication, the first step of which involves the formation of 1,1,1,2,3-pentachloropropane from 1,1,3-trichloropropene. However, the purity profile of that intermediate product is not outlined, nor is any importance attached to the purity profile of that product. In Example 2 of WO2014/130445, a 240db (1,1,1,2,3-pentachloropropane) rich material having a purity level of 96.5 to 98.5% is used.

WO2013/055894 discloses a process for producing tetrachloropropenes, particularly 1,1,2,3-tetrachloropropene and reports that the product obtained from the processes disclosed in that document have advantageously low levels of impurities which can be problematic in downstream processes for producing fluorocarbons. A discussion of the different types of impurities considered to be problematic by the authors of WO2013/055894 is set out in paragraphs [0016] and [0017] of that document.

US2012/157723 discloses a process for preparing chlorinated alkanes via a three step process. Seemingly high purity chloroalkanes appear to have been prepared according to the process disclosed in that document. However, the efficiency of the processes is not addressed and the purity data presented in the examples of that application are only given to one decimal place.

From the provision of data presented in this way, it is apparent that the analytical equipment used to measure the impurity profile of the products obtained in the examples of US2012/157723 was insensitive; conventional analytical apparatus enables hydrocarbon levels to 1 ppm (i.e. to four decimal places) to be determined. Given that one skilled in the art would need to know the impurity profile of chloroalkane feedstocks to be used in industrial scale down to a ppm level, the data presented in US2012/157723 would not be of assistance.

Despite these advances, problems can still arise through the use of chlorinated compounds obtained from the processes discussed above. Particularly, the presence of impurities, especially those which are not easily separable from the compounds of interest (e.g. as a result of similar or higher boiling points), which lead to the formation of side-products during storage, transportation, and/or use in downstream processes such as hydrofluorination, and/or which reduce the effectiveness or operating life of catalysts used in downstream processes can be problematic.

International applications Nos. WO2016/058566, WO2016/058567 and WO2016/058568 (the contents of which are incorporated herein by reference) describe processes for preparing compositions comprising $C_{3-6}$ chlorinated alkanes and alkenes having very high levels of purity in high yields, with minimal loss to side products.

A demand remains for very high purity chlorinated alkane and alkene compounds, and also for efficient, selective and reliable processes for preparing such compounds, especially enabling continuous industrial manufacture.

Demand also remains for additional processes for preparing very high purity chlorinated alkane and alkene compounds including in continuous mode, which have very low levels or are ideally free of impurities which are known or are thought to be problematic in downstream processes.

Thus, according to a first aspect of the present invention, there is provided a process for producing a reaction mixture comprising a plurality of $C_3$ chlorinated alkane isomers comprising chlorinating a $C_3$ chlorinated alkane starting material in a chlorination zone to produce the plurality of $C_3$ chlorinated alkane isomers, the plurality of $C_3$ chlorinated alkane isomers each having at least one more chlorine atom than the $C_3$ chlorinated alkane starting material, wherein the concentration of the $C_3$ chlorinated alkane starting material is controlled such that conversion of the $C_3$ chlorinated alkane to the plurality of $C_3$ chlorinated alkane isomers, represented by the molar ratio of the $C_3$ chlorinated alkane starting material:$C_3$ chlorinated alkane isomers in the reaction mixture present in the chlorination zone does not exceed about 40:60.

The process of this aspect of the present invention advantageously enables the production of a reaction mixture comprising a plurality of target $C_3$ chlorinated alkane isomers which (excluding starting materials and catalyst) preferably has a purity (i.e. content of the plurality of $C_3$ chlorinated alkane isomers) of about 98% or higher, about 98.5%, about 99%, about 99.5% or higher, about 99.7% or higher or about 99.9% or higher by weight.

For the avoidance of doubt, where the purity of a composition or material (including the plurality of $C_3$ chlorinated alkane isomers) is presented by percentage or ppm, unless otherwise stated, this is a percentage/ppm by weight.

It has been found by the inventors that it is essential to control the chlorination of the $C_3$ chlorinated alkane starting material such that the molar ratio of that starting material: plurality of isomers does not exceed about 40:60 in order to minimise the formation of problematic side products/impurities enabling the production of high grade products, even when the processes are operated in continuous mode.

The focus of many processes of the prior art is to produce compositions comprising single isomers in high purity, especially given that $C_3$ chlorinated alkane isomers are typically difficult to separate out using conventional techniques. However, it has been found by the inventors that the high purity mixtures of isomers of such compounds can be viably employed in downstream processes such as hydrofluorination, dehydrochlorination and/or isomerisation processes. Advantageously, the processes of the present invention can be operated continuously, efficiently and in a streamline manner to produce compounds having high purity levels.

For example, a plurality of chlorinated alkane isomers can viably be employed as a feedstock in the preparation of refrigerants or blowing agent components such as 1234yf, 1234zeE and/or 1233zdE. Refrigerant/blowing agent compositions comprising these components at high levels of purity are of commercial value and thus, there is significant interest in processes which can be used to reliably and efficiently provide highly pure chlorinated compounds that can be used as feedstocks to produce such compounds. The processes of this aspect of the present invention can be employed to produce two or more key feedstocks from a single production line.

Additionally or alternatively, the processes of the present invention can be used to efficiently produce high purity commercially valuable $C_3$ chlorinated compounds including 1,1,1,3,3-pentachloropropane (HCC-240fa), 1,1,3,3-tetrachloro-1-propene (HCO-1230za), 1,1,1,2,3-pentachloropropane (HCC-240db), 1,1,2,3-tetrachloro-1-propene (HCO-1230xa), 1,3,3,3-tetrachloro-1-propene (HCO-1230zd), and mixtures thereof, such as those disclosed in US2014/0221704.

One key advantage of the chlorinated alkane materials which may be obtained from the processes of the present invention is that their high purity enables them to be handled safely and with ease as the absence or acceptably low levels of impurities which could otherwise catalyse degradation over time or could interact with storage/transport vessels producing other catalysts are not present. Those chlorinated materials are therefore easier to transport, not requiring specialist measures to be taken, such as those disclosed in WO2014/120865.

The use of isomeric $C_3$ chlorinated alkane compounds is also advantageous as it simplifies production. More specifically, the use of such compositions enables multiple feedstocks to be prepared (as will be discussed below) using common upstream starting materials. As an example, if one skilled in the art wished to produce the commercially valuable chlorinated alkenes 1,1,3,3-tetrachloro-1-propene (HCO-1230za) and 1,1,2,3-tetrachloro-1-propene (HCO-1230xa), they would be aware of processes for preparing these compounds from 1,1,1,3,3-pentachloropropane (HCC-240fa) and 1,1,1,2,3-pentachloropropane (HCC-240db). However, conventionally, HCC-240fa is produced from vinyl chloride and carbon tetrachloride while HCC-240db is produced from ethylene, carbon tetrachloride and chlorine. The identification by the present inventors that multiple chlorinated alkenes can be viably and reliably produced from a single $C_3$ chlorinated alkane starting material simplifies the overall production of those chlorinated alkenes, reduces the number of starting materials and production lines, and enables the use of potentially undesirable compounds such as vinyl chloride (which is known to be highly toxic, unstable and challenging to store/transport) to be avoided. Instead, the present invention enables the use of basic starting materials (such as ethylene and chlorine) on an industrial scale to obtain the chlorinated alkenes of interest.

As a result of the advantageous processes of the present invention, the plurality of $C_3$ chlorinated alkane isomers prepared in processes of this aspect of the invention have high purity. This means that those compounds can be used themselves in downstream reactions with or without separation from each other to produce compounds which also benefit from desirable impurity profiles, minimizing the need for downstream purification steps.

For clarity, the term "plurality of $C_3$ chlorinated alkane isomers" or the like, as used herein, is not to be taken in its broadest sense—to mean any mixture in which a plurality of $C_3$ chlorinated alkane isomers are present in any amount. Those skilled in the art will consider that a mixture comprising, for example, two isomers where one of those isomers is only present in trace amounts does not include a 'plurality' for the purposes of the present invention. Thus, the term "plurality of $C_3$ chlorinated alkane isomers", or equivalent language, as used herein, means a group of $C_3$ chlorinated alkane isomers comprising at least two or more $C_3$ chlorinated alkane isomers each having the same number of chlorine and hydrogen atoms and each being present in an amount of 1% or more by weight of the total mixture of those isomers. Further, for the avoidance of doubt, any isomer present in the mixture in an amount of less than 1% by weight of the total amount of the isomers is not considered to be a component isomer of that plurality, but an impurity (an "isomeric impurity"). In preferred embodiments of the present invention, the content of such isomeric impurity/ies in the reaction mixture produced in the chlorination zone is less than about 1000 ppm, less than about 500 ppm, less than about 200 ppm, less than about 100 ppm, less than about 50 ppm, less than about 20 ppm, less than about 10 ppm or less than about 5 ppm.

Likewise, the reaction mixture preferably comprises low amounts of under chlorinated impurities (i.e. $C_3$ compound/s having one or more fewer chlorine atoms than the plurality of isomers, not including the $C_3$ starting material) for example, less than about 25000 ppm, less than about 20000 ppm, less than about 10000 ppm, less than about 5000 ppm, less than about 2000 ppm, less than about 1000 ppm, less than about 500 ppm, less than about 200 ppm, less than about 100 ppm, less than about 50 ppm, less than about ppm, less than about 10 ppm or less than about 5 ppm Additionally, the reaction mixture preferably comprises low amounts of over chlorinated impurities (i.e. $C_3$ compound/s having one or more additional chlorine atoms than the plurality of alkane isomers) for example, less than about 50000 ppm, less than about 30000 ppm, less than about 25000 ppm, less than about 20000 ppm, less than about 15000 ppm, less than about 10000 ppm, less than about 5000 ppm, less than about 2000 ppm or less than about 1000 ppm.

Further, the reaction mixture preferably comprises low amounts of compounds having a different number of carbon atoms than the isomers for example, less than about 1000 ppm, less than about 500 ppm, less than about 200 ppm, less than about 100 ppm, less than about 50 ppm, less than about 20 ppm, less than about 10 ppm or less than about 5 ppm.

Additionally or alternatively, the reaction mixture may comprise low amounts of chlorinated alkene compounds for example, less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about 5 ppm.

In embodiments of the invention, the plurality of $C_3$ chlorinated alkane isomers may comprise any number of component isomers (i.e. isomers being present in an amount of 1% or more by weight of the total plurality of isomers). For example, the plurality of $C_3$ chlorinated alkane isomers may comprise 2, 3, 4, 5, 6, 7, 8, 9 or more component isomers. In embodiments of the invention, the plurality of the $C_3$ chlorinated alkane isomers comprises two isomers, the first isomer and the second isomer.

In embodiments of the invention, the plurality of isomers is typically formed with the individual isomers not being present in a balanced ratio, i.e. the levels of each isomer will vary, with one isomer being present in a greater amount. Thus, in embodiments where the plurality of $C_3$ chlorinated alkane isomers comprises two isomers, one will be present in a greater amount than the other. In such embodiments, the ratio of isomers (e.g. the molar ratio of first isomer:second isomer or second isomer:first isomer produced in the chlorination zone may range from about 60:40, about 65:35 or about 70:30 to about 90:10, about 95:5 or about 98:2). As discussed herein, the processes of the present invention permit the ratio of the isomers to be controlled, e.g. by varying the method of catalysis and/or the type of reactor used. Thus, in alternative embodiments where a more balanced ratio of isomers is preferred, this can be achieved using processes of the present invention. In such embodiments, the molar ratio of first isomer:second isomer or second isomer:first isomer produced in the chlorination zone may range from about 40:60 to about 60:40.

The component isomers present in the plurality will each include the same number of carbon, chlorine and hydrogen atoms. Their boiling points may vary, although, owing to their structural similarity, it is envisaged that in many cases, the variations in boiling points between the component isomers present in the plurality will be relatively limited. For example, in embodiments of the invention, the boiling points of at least two of the component isomers present in the plurality will vary by ≤about 20° C., by ≤about 15° C., by ≤about 10° C. or by ≤about 5° C. In additional or alternative embodiments of the invention, the boiling point of the component isomer having the highest boiling point of all of the component isomers present in the plurality will be ≤about 20° C., ≤about 15° C., ≤about 10° C. or ≤about 5° C. higher than the boiling point of the component isomer having the lowest boiling point of all of the component isomers present in the plurality.

In embodiments of the invention, one, some or all of the $C_3$ chlorinated alkane isomers in the plurality comprises three chlorine atoms on a terminal carbon atom in the molecule.

Examples of pluralities of $C_3$ chlorinated isomers that may be prepared or employed according to processes of the present invention include i) 1,1,1,2,3-pentachloropropane and 1,1,1,3,3-pentachloropropane ii) 1,1,1,2,3-pentachloropropane and 1,1,2,2,3-pentachloropropane, and iii) 1,1,2,2,3-pentachloropropane and 1,1,1,2,2-pentachloropropane. In the isomeric pairs outlined in this paragraph, the first listed isomer may be the first isomer or the second isomer, and the second listed isomer may be the other of the first isomer or the second isomer.

Advantageously, in the processes of the present invention, the preparation of these pluralities of chlorinated alkane isomers is highly selective. The formation of over-chlorinated or under-chlorinated alkane impurities is minimal, as is the formation of pentachloropropane isomers other than the isomers of interest.

In processes of the present invention, for example group i) may be prepared by chlorinating 1,1,1,3-tetrachloropropane. Group ii) may be prepared by chlorinating 1,2,3-trichloropropane, 1,2,2,3-tetrachloropropane, 1,1,2,3-tetrachloropropane or a mixture of 1,1,2,3-tetrachloropropane and 1,2,2,3-tetrachloropropane. Group iii) may be prepared by chlorinating 1,2-dichloropropane or 1,1,2,2-tetrachloropropane and 1,2,2,3-tetrachloropropane. Any of these compounds or mixtures thereof may be employed as starting materials in processes of the present invention.

A further advantage of the process of the present invention is that the formation of impurities which may be problematic in downstream processes is limited, or ideally prevented. For example, the formation of impurities arising from the serial chlorination of compounds present in the reaction mixture is prevented by controlling the level of $C_3$ chlorinated alkane starting material present in the mixture in the chlorination zone.

Thus, for example, where the chlorinated alkane isomers present in the reaction mixture formed in the chlorination step employed in the process of this aspect of the present invention include one more chlorine atom than the chlorinated alkane starting material, the production of compounds including two or more chlorine atoms than the starting material is restrained.

In such embodiments, the reaction mixture present in the chlorination zone may comprise less than about 5%, less than about 2%, less than about 1%, less than about 0.5%, less than about 0.2%, less than about 0.1%, less than about 0.05%, less than about 0.02%, or less than about 0.01% of compounds including two or more chlorine atoms than the $C_3$ chlorinated alkane starting material.

The inventors have found that, under certain operating conditions, maintaining the molar ratio of the $C_3$ chlorinated alkane starting material:$C_3$ chlorinated alkane isomers obtained by the chlorination of the $C_3$ chlorinated starting material in the reaction mixture present in the chlorination zone such that it does not exceed 40:60, i.e. the conversion of the $C_3$ chlorinated alkane starting material to the plurality of isomers is limited to 60%, plays a significant role in preventing serial chlorination of the starting material which would otherwise lead to the formation of highly reactive materials. For the avoidance of doubt, in the present application, where reference is made to controlling or limiting a molar ratio of starting material:product such that it does not exceed a specified level, this means that the conversion of the starting material to the specified product is limited to the level specified in the given ratio.

In embodiments of the invention, the molar ratio of the $C_3$ chlorinated alkane starting material:$C_3$ chlorinated alkane isomers in the reaction mixture present in the chlorination zone/extracted therefrom may be maintained in the range of about 99:1, about 97:3, about 95:5 to about 90:10, about 85:15 about 80:20 or about 75:25. Alternatively, the molar ratio of the $C_3$ chlorinated alkane starting material:$C_3$ chlorinated alkane isomers in the reaction mixture present in the chlorination zone/extracted therefrom may be maintained in the range of about 90:10, about 80:20, or about 70:30 to about 65:35, about 60:40 or about 55:45. In alternative embodiments, the ratio may be about 90:10, about 80:20, about 70:30, to about 60:40, about 50:50 to about 40:60. Example 8 confirms the effect of the degree of conversion of the starting material to the isomers of interest on the formation of impurities.

As those skilled in the art will appreciate, while control over the chlorination process is characterised herein in terms of the molar ratio between starting material and the isomeric product, it can also considered as control over the conversion of starting material to product—thus a molar ratio of starting material:isomeric product of 75:25 equates to a conversion of 25%. The inventors have found that limiting the conversion of the starting material as outlined above minimises the formation of undesirable impurities.

Any technique or equipment may be used by those skilled in the art to determine the composition of the reaction mixture present in the chlorination zone. For example, a direct determination of the reaction mixture can be made e.g.

by providing the chlorination zone with a port through which samples of the reaction mixture can be extracted for analysis. Additionally or alternatively, reaction mixture is extracted from the chlorination and subjected to further treatment steps. In such embodiments, samples of reaction mixture may be taken upon extraction of that reaction mixture from the chlorination zone, e.g. via a port located at or in the vicinity of the outlet of the chlorination zone. Additionally or alternatively, an indirect determination of the composition can be made e.g. by temperature control as temperature is a function of composition at constant pressure. The determination of the composition should be made at the point at which the reaction mixture is extracted from the chlorination zone, or, in embodiments in which the $C_3$ chlorinated alkane isomers are extracted directly from the reaction mixture in the reaction zone at the point at which that extraction occurs.

The problem of serial chlorination of the starting material is addressed by the processes of the present invention. More specifically, International Patent Application No. WO98/05614 discloses the formation of mixtures of $C_3$ chlorinated alkane isomers, specifically 1,1,1,3,3-pentachloropropane and 1,1,1,2,3-pentachloropropane. However, the inventors, having reproduced the examples of WO98/05614 have found that the processes disclosed in that document inevitably result in the formation of hexachloropropanes, especially 1,1,1,3,3,3-hexachloropropane. This serial chlorination product has a very close boiling point to 1,1,1,2,3-pentachloropropane (240db) making its separation from the pentachloropropane of interest challenging. Further, it is very unstable in the presence of metals and thus produces further degradation products (such as 1,1,3,3,3-pentachloropropene) during downstream processing steps such as distillation and/or at elevated temperatures.

The present inventors have identified that by limiting the molar ratio of $C_3$ chlorinated alkane feedstock (e.g. 1,1,1,3-tetrachloropropane) and the resulting pentachloropropane isomers in the chlorination zone to 40:60, the formation of the over chlorinated side products such as unstable 1,1,1,3,3,3-hexachloropropane is minimised.

The level of the chlorinated alkane starting material in the reaction mixture may be controlled by, for example, i) removing the $C_3$ chlorinated alkane isomers (by extracting reaction mixture and/or by extracting a $C_3$ chlorinated alkane rich stream, e.g. via direct distillation) from the chlorination zone, ii) by controlling the reaction conditions in the chlorination zone (e.g. temperature, exposure to light, catalyst concentration and/or pressure), and/or iii) by controlling the amount of chlorinated alkane starting material and/or chlorine present in the chlorination zone.

This list is not exhaustive; any method or technique can be utilised to control the reaction rate, so that the formation of over chlorinated impurities and/or serial adducts to higher adduct compounds can be avoided.

In embodiments of the present invention, reaction mixture may be extracted from the chlorination zone and/or subjected to direct distillation (i.e. where distillation apparatus is in direct communication with the chlorination zone). In such embodiments, owing to control over the conversion of the starting material to the plurality of isomers, the reaction mixture which is extracted from the chlorination zone and/or subjected to direct distillation has a molar ratio of the $C_3$ chlorinated alkane starting material:$C_3$ chlorinated alkane isomers as outlined above, i.e. which does not exceed 40:60 or which, in certain embodiments may have narrower ranges, again, as outlined above.

The rate of agitation or stirring of the chlorination zone can additionally or alternatively be reduced to retard the chlorination process.

In embodiments of the invention in which the degree of conversion of the chlorinated alkane starting material to the chlorinated alkane isomers of interest is controlled (i.e. limited) by controlling the amount of chlorine present in the chlorination zone, the chlorine content in the reaction mixture extracted from the chlorination zone may be very low, for example about 1% or less, about 0.5% or less, about 0.1% or less, about 0.05% or less or about 0.01% or less.

Additionally, or alternatively, to control the degree of conversion of the starting material to the isomers of interest, the amount of molecular chlorine provided into the chlorination zone may substoichiometric as compared to the $C_3$ chlorinated alkane starting material. For example, the amount of molecular chlorine provided into the chlorination zone may be about 5%, about 10%, about 15% or about 20% to about 25%, about 30%, about 35%, about 40%, about 50%, about 60%, or about 70%, of the moles of $C_3$ chlorinated alkane starting material provided to the chlorination zone.

In embodiments of this aspect of the invention, the starting material is a $C_3$ chlorinated alkane comprising 1, 2, 3, 4, 5 or 6 chlorine atoms. In the chlorination step employed in the process of this aspect of the present invention, the $C_3$ chlorinated alkane starting material may be converted to a plurality of isomers having the same number of carbon atoms as the starting material, and 1, 2, 3 or more chlorine atoms than the starting material.

The $C_3$ chlorinated alkane starting material preferably has a high degree of purity. For example, the starting material may have a purity of about 98% or higher, about 98.5% or higher, about 99% or higher, about 99.5% or higher, about 99.7% or higher, about 99.9% or higher. Processes for preparing such compositions and such compositions with defined impurities are disclosed in W2016/058566, the contents of which are incorporated herein by reference.

While $C_3$ chlorinated alkane starting materials employed in the process of this aspect of the present invention may be obtained from any synthetic route, it is generally preferred that the starting material is not obtained from a route employing a chlorinated alkene (e.g. vinyl chloride) as a starting material. This is because the $C_3$ chlorinated alkane starting material may comprise residual amounts of chlorinated alkene (e.g. vinyl chloride) which is problematic as chlorinated alkenes (e.g. vinyl chloride) are toxic and may also polymerise to form polymers (e.g. polyvinylchloride) that can cause reactor clogging in downstream processes. Vinyl chloride monomers are also challenging to store/transport and have safety issues, thus the avoidance of the use of starting materials which are free of such monomers is preferable.

Thus, in embodiments of this aspect of the present invention, the $C_3$ chlorinated alkane starting material is obtained from chlorinated alkene-free (e.g. vinyl chloride-free) processes (i.e. processes not employing chlorinated alkenes such as vinyl chloride as a reactant) and/or which comprise less than about 1000 ppm, less than about 500 ppm, less than about 200 ppm, less than about 100 ppm, less than about 50 ppm, less than about ppm, less than about 10 ppm, less than about 5 ppm or less than about 2 ppm chlorinated alkene (e.g. vinyl chloride).

Examples of processes for producing such a starting material are disclosed in W2016/058566, the contents of which are incorporated herein by reference. The processes provided in those applications enable high purity $C_3$ chlorinated alkanes to be produced.

Such feedstocks, whether produced according to such processes or not, may be employed as starting materials in the processes of the present invention and which may comprise:

- less than about 2000 ppm, less than about 1000 ppm, less than about 500 ppm, less than about 200 ppm or less than about 100 ppm or less than 50 ppm chlorinated alkane impurities (i.e. chlorinated alkane compounds other than the chlorinated $C_3$ alkane starting material), e.g. chlorobutane,
- less than about 2000 ppm, less than about 1000 ppm, less than about 500 ppm, less than about 200 ppm or less than about 100 ppm, or less than about 50 ppm, or less than ppm chlorinated alkene compounds, e.g. perchloroethylene,
- less than about 2000 ppm, less than about 1000 ppm, less than about 500 ppm, less than about 200 ppm or less than about 100 ppm or less than about 50 ppm, or less than ppm oxygenated organic compounds,
- less than about 2000 ppm, less than about 1000 ppm, less than about 500 ppm, less than about 200 ppm or less than about 100 ppm brominated compounds,
- less than about 1000 ppm, less than about 500 ppm, less than about 200 ppm, less than about 100 ppm, less than about 50 ppm or less than about 20 ppm of water,
- less than about 500 ppm, less than about 200 ppm, less than about 100 ppm, less than about 50 ppm or less than about 20 ppm metallic catalyst, and/or
- less than about 500 ppm, less than about 200 ppm, less than about 100 ppm, less than about 50 ppm or less than about 20 ppm catalyst promoter.

Advantageously, in embodiments of the invention, the use of $C_3$ chlorinated alkane starting materials having one trichlorinated terminal carbon atom minimises the number of chlorinated alkane isomers which are formed. Thus, in embodiments of the invention, the $C_3$ chlorinated alkane starting material is a compound having a trichlorinated terminal carbon atom.

In embodiments of the present invention, the $C_3$ chlorinated alkane starting material may be 1,1,1,3-tetrachloropropane (which, in embodiments of the invention, may be obtained from carbon tetrachloride and ethylene), mixture of 1,1,2,3-tetrachloropropane and 1,2,2,3-tetrachloropropane (which may be obtained from 1,2,3-trichloropropane from 3-chloropropene), 1,1,2,3-tetrachloropropane (which may be obtained from 1,3-dichloropropene), mixture of 1,1,2,2-tetrachloropropane and 1,2,2,3-tetrachloropropane (which may be obtained from 1,2,2-trichloropropane from 2-chloropropene or from 1,2-dichlorpropane). In embodiments where 1,1,1,3-tetrachloropropane is employed as the $C_3$ chlorinated alkane starting material, that material preferably comprises levels of per chlorinated ethylene, chlorinated butyl compounds and iron residues within the limits outlined above.

In embodiments of this aspect of the present invention, chlorination of the $C_3$ chlorinated alkane starting material may be carried out by reacting the starting material with chlorine. For example, this may be achieved by contacting the chlorine and the $C_3$ chlorinated alkane starting material in the chlorination zone by those reactants being fed into that zone using any technique or equipment known to those skilled in the art, for example via dispersion devices such as tube/s (e.g. dip tube/s), nozzle/s, porous plates, ejectors, static mixing devices and/or sparger/s. In such embodiments, the feed of chlorine and/or $C_3$ chlorinated alkane starting material may be continuous or intermittent. The chlorine supplied as a feed into the chlorination zone in which the reaction mixture is present may be in liquid and/or gaseous form. Likewise, the $C_3$ chlorinated alkane starting material may be in liquid and/or gaseous form. The chlorination zone may be fed with one or more chlorine feeds. Additional vigorous stirring may be used to ensure good mixing and/or dissolution of the chlorine into the liquid reaction mixture.

Where the reaction mixture in the chlorination zone is liquid, the chlorine may be fed into the chlorination zone as gas into the headspace of the chlorination zone. Additionally, or alternatively, the chlorine may be fed into the reaction mixture, a solvent, a process intermediate and/or the feed stream of the $C_3$ starting material upstream of the chlorination zone and dissolved or entrained therein.

In embodiments of the present invention, the reaction conducted in the chlorination zone is in the liquid phase, i.e., the reaction mixture present therein is predominantly or totally liquid. The reaction mixture may be analysed using any techniques known to those skilled in the art e.g. chromatography.

The chlorine used as a starting material in the processes of the present invention is preferably highly pure. In embodiments of the invention, the chlorine preferably has a purity of at least about 95%, at least about 97%, at least about 99%, at least about 99.5%, or at least about 99.9%

Additionally or alternatively, the chlorine used in the processes of the present invention may comprise bromine or bromide in an amount of about 200 ppm or less, about 100 ppm or less, about 50 ppm or less, about 20 ppm or less or about 10 ppm or less.

The use of chlorine gas comprising low amounts of oxygen (e.g. about 200 ppm or less, about 100 ppm or less, about 50 ppm or less, about 20 ppm or less or about 10 ppm or less) is also envisaged. However, in embodiments of the present invention, lower grade chlorine (including higher oxygen levels, e.g. of 1000 ppm or higher) can be employed without the final product of the processes of the present invention comprising unacceptably high levels of oxygenated impurities.

In embodiments of the present invention, chlorine content within the chlorination zone is controlled as this has been found to minimise the formation of side products. In such embodiments, it is preferable if the chlorination zone is equipped with monitoring means to detect chlorine levels within the chlorination zone and/or at the reactor outlet.

In embodiments of the present invention, chlorination of the $C_3$ chlorinated alkane starting material may be catalyzed. For example, chlorination may be carried out under exposure to UV and/or visible light ("photochlorination"). For example, this may be achieved by including a UV and/or visible light source in the chlorination zone, e.g. glass tubes for light introduction within the chlorination zone. Additionally or alternatively, a wall in the reactor may be transparent enabling the passage of UV and/or visible light into the chlorination zone within the reactor. In embodiments, exposure of the reaction mixture to light (for example ultra violet light) promotes the reaction when operated at low temperatures.

In embodiments in which photochlorination is carried out, light flux, power and wavelength into the chlorination zone is preferably controlled.

Additionally or alternatively, chlorination of the $C_3$ chlorinated alkane starting material may be catalyzed by Lewis acid type catalysts such as metal and/or hybrid metal catalysts. Examples of such catalysts include one or more halides (e.g. chlorides, bromides, fluorides or iodides) of transition metals such as iron, aluminium, antimony, lanthanum, tin, titanium, or boron or elements such as sulphur or iodine. Specific examples of catalysts that may be employed include $FeCl_3$, $AlCl_3$, $SbCl_5$, $SnCl_4$, $TiCl_4$, $BF_3$, $SO_2Cl_2$ and/or metal triflate. Ferric chloride can be also prepared in-situ by means of the direct or indirect addition of iron catalyst precursor (for example solid iron) into the reaction mixture.

Such catalysts, where used, may be employed in any quantity, provided that effective catalysis of the reaction. However, in embodiments of the invention, relatively low amounts of catalyst may be used, for example, less than 1000 ppm, less than 750 ppm, less than 500 ppm, less than 400 ppm, less than 300 ppm, less than 200 ppm, less than 150 ppm or less than 100 ppm, to more than about 2 ppm, more than about 5 ppm, more than about 7 ppm or more than about 10 ppm The inventors have unexpectedly found that the type of catalysis used during chlorination influences the ratio of $C_3$ chloroalkane isomers that are produced. Generally speaking, where photochlorination is used in the absence of other catalysts such as Lewis acid catalysts, this favours the formation of a first chlorinated alkane isomer, while if a Lewis acid catalyst is used in combination with UV/visible light, this favours the formation of a second chlorinated alkane isomer. In embodiments of the present invention, therefore, the chlorination reaction is catalyzed (or promoted) using only UV and/or visible light in order to achieve selectivity in favour of a first isomer over a second isomer of about 60%, about 70% or about 75%. In alternative embodiments, a combination of Lewis acid and UV and/or visible light is used to catalyse the chlorination reaction in order to achieve selectivity in favour of a second isomer over a first isomer of about 60%, about 70%, about 80%, about 90% or about 95%.

Thus, in embodiments of the present invention, chlorination of the $C_3$ chlorinated alkane starting material is promoted/catalysed by i) exposure to UV/visible light and ii) Lewis acid. In such embodiments, the process additionally comprises the step of controlling i) the duration and/or extent of exposure to, wavelength of, flux of and/or power of the UV/visible light, and/or ii) the concentration of Lewis acid in the reaction mixture.

As an example of such a system, the inventors have successfully controlled the molar ratio of 1,1,1,3,3-pentachloropropane and 1,1,1,2,3-pentachloropropane from 80:20 (using only exposure to UV light), through 70:30, 60:40, 50:50, 40:60, finishing 2:98 (using the combination of promoted/catalysed chlorination comprising UV and Lewis acid). This approach enables the production of chlorinated alkane isomers at predetermined ratios and also selectively, such that non-target pentachloropane isomers are not formed.

As is demonstrated in the examples that follow, other reaction conditions which influence the molar ratio of isomers formed in the processes of the present invention additionally include residence time of the reaction mixture in the chlorination zone as well as operating temperature within the chlorination zone.

Thus, in embodiments of the invention, the mean residence time of the reaction mixture in the chlorination zone may be about 60 minutes or less, about 45 minutes or less, about 30 minutes or less, about 20 minutes or less, about 15 minutes or less or about 10 minutes or less. Alternatively, the mean residence time of the reaction mixture in the chlorination zone may be about 60 minutes or more, about 75 minutes or more, about 90 minutes or more, or about 120 minutes or more. In embodiments of the invention, the mean residence time of the reaction mixture in the chlorination zone may be from about 10 minutes to about 40 minutes, from about 40 minutes to about 80 minutes, or about 80 minutes or longer.

Additionally or alternatively, the operating temperature of the chlorination zone may be about 60° C. or less, about 45° C. or less, about 30° C. or less, about 20° C. or less, about 15° C. or less or about 10° C. or less. Alternatively, the operating temperature of the chlorination zone may be about 60° C. or more, about 75° C. or more, about 90° C. or more, or about 120° C. or more. In embodiments of the invention, the operating temperature of the chlorination zone may be from about 10° C. to about 40° C., from about 40° C. to about 80° C., or 80° C. or above.

In embodiments of the present invention, where chlorination of the $C_3$ chlorinated alkane starting material results in the formation of first and second $C_3$ chlorinated alkane isomers, those isomers are present in a molar ratio of about 95:5, about 90:10, about 80:20, about 70:30, about 60:40, about 50:50, about 40:60, about 30:70, about 20:80, about 10:90, or about 5:95 to about 5:95, about 10:90, about 20:80, about 30:70, about 40:60, about 50:50, about 60:40, about 70:30, about 80:20, about 90:10 or about 95:5.

Chlorination may be carried out at any temperature which enables the conversion of the starting material to the chlorinated alkane isomers of interest. Optimal temperatures will depend on the specific chlorinated alkane starting material which is employed and/or the degree of chlorination that is required (e.g. the number of chlorine atoms to be added to the starting material).

In embodiments of the invention, it has been found that relatively mild reaction conditions enable the progress of the reaction to be controlled, while enabling the chlorination reaction to proceed at an acceptable rate and minimizing the production of unwanted impurities, such as over-chlorinated impurities. For example, operating temperatures within the range of about −30° C., about −20° C., about −10° C., about 0° C. or about 20° C. to about 40° C., about 60° C., about 80° C., about 100° C., about 120° C., about 150° C., about 170° C. or about 200° C. may be employed in the chlorination zone.

Depending on the type of reactor, the intended molar ratio of the plurality of isomers, the starting material and/or the type of catalysts to be used the chlorination step in the processes of the present invention may be carried out at a low temperature range (e.g. about −30° C., about −20° C., about −10° C. to about 10° C., about 20° C. or about 30° C.) at a moderate temperature range (e.g. about −30° C., about −20° C., about −10° C., about 0° C., about 10° C., about 20° C. or about 30° C. to about 50° C., about 70° C. or about 100° C.), or at a higher temperature range (e.g. about 50° C., about 70° C., about 90° C. or about 110° C. to about 150° C., about 170° C. or about 200° C.).

As purely illustrative examples, the inventors have found that chlorination reactions catalyzed by UV and/or visible light only can be operated at a low temperature range as outlined above, while chlorination reactions catalysed only by Lewis acid catalysts can be operated at a higher temperature range as outlined above. In arrangements where chlorination reactions of the present invention are catalyzed by UV and/or visible light and Lewis acids, a moderate temperature range may be employed.

The inventors have found that by operating the chlorination reaction at such temperatures in, e.g. a continuous mode, an advantageous balance is reached between good reaction efficiency and reduction in the formation of unwanted impurities.

The chlorination zone may be operated at subatmospheric pressure, atmospheric pressure or superatmospheric pressure.

Any type of reactor which can provide a chlorination zone in which the chlorination of $C_3$ chlorinated alkane starting material to produce a reaction mixture comprising $C_3$ chlorinated alkane isomers can be achieved may be employed in the processes of the present invention. Specific examples of reactors that may be used in the processes of the present invention to provide the chlorination zone are column reactors (e.g. column gas-liquid reactors), tubular reactors, bubble column reactors, plug/flow reactors (e.g. tubular plug/flow reactors) and stirred tank reactors (e.g. continuous stirred tank reactors) and photoreactors (such as falling film photoreactors).

The process of the present invention may be carried out in a single chlorination zone or in a plurality of chlorination zones. Where a plurality of chlorination zones are employed (for example, 2, 3, 4, 5, 6 or more chlorination zones), these may be operated in sequence (i.e. such that reaction mixture is passed along a number of chlorination zones) and/or in parallel. In embodiments of the invention, chlorination of the starting material is achieved in a series of continuously stirred tank reactors operated in sequence.

In embodiments in which photochlorination of the $C_3$ chlorinated alkane starting material is carried out, the reactor is preferably provided with a source of UV and/or visible light and/or a port through which light can pass into the chlorination zone. Where a solid (e.g. particulate) catalyst (e.g. a Lewis acid catalyst) or liquid catalyst is employed, this may be fed directly into the chlorination zone. Additionally or alternatively, this may be dissolved or dispersed in the $C_3$ chlorinated alkane starting material upstream of the chlorination zone.

Those skilled in the art will recognise that where different types of reactors are used, operating conditions and/or the degree of conversion of the $C_3$ chlorinated alkane starting material to the chlorinated alkane isomeric product may be modified to optimise the chlorination process. As a purely illustrative example, in a continuous chlorination process in which UV and/or visible light is used to catalyse the reaction (e.g. in which the chlorination zone is provided in a continuously stirred tank photoreactor) with standard vacuum distillation being employed, the molar ratio of $C_3$ chlorinated alkane starting material:$C_3$ chlorinated alkane isomers may be limited to 60:40 and/or the operating temperature of the chlorination zone may be within the range of about 30° C. to about 30° C. In alternative arrangements, in which a circulation or loop reactor is used to provide the chlorination zone and the reaction mixture is subjected to direct distillation, the molar ratio of $C_3$ chlorinated alkane starting material:$C_3$ chlorinated alkane isomers may be limited to 90:10 and/or the operating temperature of the chlorination zone may be as high as about 120° C. In a still further embodiment, in which a photoreactor, for example a falling film tubular photoreactor is used, the molar ratio of $C_3$ chlorinated alkane starting material:$C_3$ chlorinated alkane isomers may be limited to 40:60.

Reactors used in the present invention may be divided into different zones each having different flow patterns and/or different operating temperatures/pressures. For example, the chlorination step may be performed in a reactor including a plurality of reaction zones. Those zones may be operated at different temperatures and/or pressures.

Additionally or alternatively, reactors used in the processes of the present invention may be provided with external circulation loops. The external circulation loops may optionally be provided with cooling and/or heating means- and/or with devices for selective extraction/removal of the chlorinated alkane isomers from the chlorination zone.

As those skilled in the art will recognise, the chlorination zone can be maintained at target temperatures through use of cooling/heating elements such as cooling tubes, cooling jackets, cooling spirals, heat exchangers, heating fans, heating jackets or the like. In embodiments in which photochlorination is carried out and UV and/or visible light is supplied to the chlorination zone using glass tube, the tube may additionally be configured to enable the flow therethrough of a coolant (e.g. water).

The operating temperature in the chlorination zone may be controlled by any temperature control means known to those skilled in the art, for example heating and/or cooling means such as heating/cooling jackets, heating/cooling loops either internal or external to the reactor, cooling spirals, heat exchangers, heating fan and the like. Additionally or alternatively, the temperature may be controlled by controlling the temperature of material/s added into the chlorination zone, thus, controlling the temperature of the reaction mixture therein. The reaction mixture is maintained in the chlorination zone for a time and under conditions sufficient to achieve the required level of conversion of the chlorinated alkane starting material to the chlorinated alkane isomers.

Those skilled in art will recognise that, in certain embodiments, the reaction zones utilised at any stage in the processes of the present invention (e.g. chlorination and/or dehydrochlorination) may employ agitation means, e.g. stirrers, followers, flow channeling means or the like.

As mentioned above, the proportion of the chlorinated alkane starting material present in the reaction mixture present in the chlorination zone can be controlled by extracting the isomers of interest from the chlorination zone. This extraction may be carried out on a batch-wise or continuous basis. For the avoidance of doubt, where reference is made in the present application to the continuous extraction of material from the zones employed in the processes of the present invention, this should not be assigned a purely literal meaning. One skilled in the art would recognise that, in such embodiments, reaction mixture may be removed on a substantially continuous basis while the chlorination zone is at operating conditions and, if its purpose is to set up a steady state reaction, once the reaction mixture therein has attained the required steady state.

Separation of the isomers of interest from the reaction mixture present in the chlorination zone can be achieved using any technique known to one skilled in the art. For example, one or more distillation steps may be employed.

The reaction mixture produced in the chlorination zone will comprise unreacted $C_3$ chlorinated alkane starting material, a plurality of $C_3$ chlorinated alkane isomers, and potentially impurities such as those outlined above, e.g. isomeric impurities, under-chlorinated impurities, over-chlorinated impurities, compounds having a different number of carbon atoms than the isomers and/or chlorinated alkene isomers.

In embodiments where post-chlorination distillation is conducted, one or more distillation steps may be performed. Such steps may be performed directly on reaction mixture present in the chlorination zone and/or on reaction mixture extracted from the chlorination zone before and/or after any post-chlorination treatment steps such as an aqueous treatment step.

Post-chlorination distillation results in a plurality of $C_3$ chlorinated alkane isomer stream being obtained which is rich in or consists of the target plurality of isomers (e.g. 1,1,1,2,3-pentachloropropane and 1,1,1,3,3-pentachloropropane).

Additionally, one or more of the following streams may be obtained:

- unreacted $C_3$ chlorinated alkane starting material (e.g. 1,1,1,3-tetrachloropropane) stream which is rich in or consists of the $C_3$ chlorinated alkane starting material,
- one or more single isomer streams rich in or consisting of one of the target isomers (e.g. 1,1,1,2,3-pentachloropropane or 1,1,1,3,3-pentachloropropane) where, owing to the boiling points of the isomers and/or distillation conditions it is possible to selectively distil at least a proportion of one of the isomers.
- one or more distillation residue streams rich in or consisting of under chlorinated impurities, over chlorinated impurities and/or impurities having a different number of carbon atoms to the isomers.

Those skilled in the art will recognize that streams said to be rich in particular compounds (or pluralities of such compounds) will comprise the specified compounds as the principal components, i.e. they will contain at least 50% of the specified compound/s. In preferred embodiments, one, some or all of the above-mentioned streams comprise at least about 80%, at least about 90%, at least about 95%, at least about 97%, at least about 99%, at least about 99.5%, or at least about 99.9% of the specified compound/s.

For the avoidance of doubt, as used herein the term 'stream' should be interpreted broadly, thus encompassing portion/s of compound extracted from a reaction mixture with at least some degree of selectivity using a distillation technique or the like, regardless of whether, owing to the distillation technique in question, those portion/s are actually collected as fractions or streams.

In preferred embodiments, the plurality of $C_3$ chlorinated alkane isomer stream and/or the one or more single isomer stream/s, where obtained, comprise:

- less than about 10000 ppm, less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about 5 ppm of under chlorinated impurities,
- less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about ppm of over chlorinated impurities,
- less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about ppm of chlorinated alkene compounds,
- less than about 1000 ppm, less than about 500 ppm, less than about 200 ppm, less than about 100 ppm, less than about 50 ppm, less than about 20 ppm, less than about ppm or less than about 5 ppm of compounds having a different number of carbon atoms than the isomers,
- less than about 1000 ppm, less than about 500 ppm, less than about 200 ppm, less than about 100 ppm, less than about 50 ppm, less than about 20 ppm, less than about ppm less than about 5 ppm, or less than about 2 ppm of oxygenated organic impurities,
- less than about 500 ppm, less than about 200 ppm, less than about 100 ppm, less than about 50 ppm, less than about 20 ppm, less than about 10 ppm or less than about ppm metal, and/or
- less than about 100 ppm, less than about 50 ppm, less than about 20 ppm, less than about 10 ppm or less than about 5 ppm water.

For the avoidance of doubt, one some or all of the streams outlined above may be obtained in the same or different distillations. For example, all four of the streams may be obtained in a single distillation step employing distillation apparatus that enables multiples streams of distillate to be obtained simultaneously or sequentially.

Alternatively, each of the streams outlined above may be collected individually in separate distillation steps.

As a further alternative, one of the streams mentioned above may be obtained in a first distillation step, for example one which may be conducted directly on reaction mixture present in the chlorination zone. The reaction mixture may then be fed to distillation apparatus remote from the chlorination zone and subjected to a single or multiple distillation steps to one or more of the other streams mentioned above.

In one embodiment, whether a single or multiple post-chlorination steps are conducted, a single isomer stream may be collected. One skilled in the art will recognize that in embodiments where a single isomer stream is distilled from the mixture, this will affect the ratio of isomers present in the plurality of isomers in the mixture.

This, alongside the optional selection of chlorination catalysts as discussed above, enables the ratio of the isomers present in the plurality to be carefully controlled such that the optimal isomeric ratio for the downstream processing application can be achieved.

Thus, in embodiments of the invention, a single isomer may be separated from a mixture containing a plurality of isomers having a first isomeric ratio, resulting in the isomeric ratio of that plurality of isomers in the mixture being altered in favour of the other isomer/s remaining in the mixture. For example, in such embodiments, the proportion of the other isomer/s remaining in the mixture may be increased by at least about 2%, about 5%, about 7%, about 10%, about 15%, about 25%, or about 50%.

Put another way, in embodiments of the invention in which the plurality of $C_3$ chlorinated alkane isomers consists of a pair of isomers, a first and a second isomer, distillation of the mixture to obtain a single isomer stream rich in or consisting of the second isomer will increase the proportion of the first isomer in the plurality of $C_3$ chlorinated alkane isomers. Alternatively, where distillation of the mixture to obtain a single isomer stream rich in or consisting of the first isomer is carried out, this will increase the proportion of the second isomer in the plurality of $C_3$ chlorinated alkane isomers. In such embodiments, the proportion of the first or second isomer in the plurality of isomers is increased by about 3% or more, by about 5% or more, by about 10% or more, or by about 20% or more.

In such embodiments, the single isomer stream may be obtained before any other streams are obtained from the mixture. This may be achieved using separate distillation apparatus from that used to obtain the plurality of $C_3$ chlorinated alkane isomer stream and any other streams. Alternatively, the same apparatus may be used, with the single isomer stream being obtained prior to or simultaneously with the plurality of $C_3$ chlorinated alkane isomer stream and any other streams being obtained.

Where obtained, the unreacted $C_3$ chlorinated alkane starting material stream may be fed back in to the chlorination zone. Additionally or alternatively, the plurality of $C_3$ chlorinated alkane isomer stream and/or the single isomer stream/s (if obtained) may be subjected to downstream processing steps, e.g. the selective dehydrochlorination process discussed below.

In embodiments of the invention, the $C_3$ chlorinated alkane starting material stream is obtained by direct distillation using distillation apparatus in communication with the chlorination zone. In such embodiments, the reaction mixture may then be extracted from the chlorination zone/direct distillation apparatus and subjected to downstream distillation steps and/or other processing steps. Those skilled in the art will recognize that in such embodiments, distillation of the $C_3$ chlorinated alkane starting material stream will result in the proportion of the plurality of $C_3$ chlorinated alkane isomers present in the mixture being increased, potentially beyond the molar ratio limit of 60%.

The distillation residue stream/s may be discarded and/or subjected to further treatment steps such as incineration or high temperature chlorinolysis (to produce useful materials (e.g. carbon tetrachloride which can be used to produce the starting chlorinated alkane 1,1,1,3-tetrachloropropane, for example via the processes disclosed in W2016/058566 and/or tetrachloroethene) at high purity).

Separation of the impurities included in this stream from the target isomers is preferable owing to the negative influence of the reactive impurities including over chlorinated impurities (e.g. 1,1,1,3,3,3-hexachloropropane) in downstream conversion steps, for example in dehydrochlorination steps as these can produce further undesired impurities which will contaminate the final products of interest.

As mentioned herein, one of the advantages provided by the present invention is that the plurality of $C_3$ chlorinated alkane isomers are produced at high levels of purity meaning that less purification steps are required to obtain high quality feedstocks that can be used in downstream processes (such as hydrofluorination reactions) as compared to processes of the prior art. Accordingly, in embodiments of the invention, the number of distillation steps that are performed on the $C_3$ chlorinated alkane isomers following the chlorination of the $C_3$ chlorinated alkane starting material and prior to those isomers being used in a downstream chemical conversion reaction (e.g. dehydrochlorination) is limited to 3, 2 or 1.

As mentioned above, distillation of the reaction mixture may be direct distillation, i.e. where the distillation apparatus is in direct communication with the chlorination zone enabling the reaction mixture to be passed directly into the distillation apparatus.

Additionally or alternatively, reaction mixture may be extracted from the chlorination zone before being fed into distillation apparatus remote from the chlorination zone.

Any distillation apparatus or techniques which can be used to selectively extract a stream rich in the $C_3$ chlorinated alkane isomers of interest from the reaction mixture present in the chlorination zone may be employed.

As an example of an arrangement which may be used to distill reaction mixture to produce a $C_3$ chlorinated alkane isomer rich stream, a "circulation" or "loop" chlorination reactor can be employed, in which reaction mixture is continuously removed from the reaction zone and treated using a distillation device, preferably operated under vacuum, located in the external circulation. In the distillation device, the $C_3$ chlorinated alkane starting material is distilled off and fed back to the chlorination zone while the isomer mixture is the distillation residue which is taken forward for further processing, for example one or more distillation steps conducted in distillation apparatus remote from the reactor in which $C_3$ chlorinated alkane isomer stream/s, single isomer stream/s and or distillation residue stream/s are obtained. The use of such apparatus advantageously suppresses serial reactions which otherwise would lead to the formation of over chlorinated side products and can utilize some or all of the heat of reaction which can advantageously reduce operating cost.

In embodiments of the invention, distillation to obtain one some or all of the streams mentioned above can be achieved in a single distillation apparatus, for example a batch distillation system comprising, e.g. a batch column, a boiler, a condenser and distillate tanks. Alternatively, one some or all of those streams could be obtained using a series of continuous distillation systems comprising, e.g. columns, boilers, condensers, and distillate tanks.

It has been found that, under certain operating conditions, the use of high distillation temperatures can lead to the formation of unwanted impurities. Thus, where distillation step/s are employed in the processes of the present invention, distillation may be conducted at a temperature of (i.e. the liquid being subjected to distillation is not exposed to temperatures greater than) about 130° C. or less, about 120° C. or less, about 110° C. or less, about 105° C. or less, about 100° C. or less, about 90° C. or less or about 80° C. or less.

To facilitate distillation at modest temperatures, distillation may be carried out at reduced pressure. For example, distillation may be conducted under vacuum. Where vacuum distillation is carried out, the vacuum conditions may be selected such that the distillation may be conducted at a low temperature.

As mentioned above, any distillation equipment known to those skilled in the art can be employed in the processes of the present invention, for example a distillation boiler/column arrangement. However, it has unexpectedly been found that the formation of chlorinated alkane degradation products can be minimised if distillation apparatus formed of certain materials are avoided.

In embodiments of the invention in which mixtures comprising chlorinated alkane compounds are subjected to one or more distillation steps, the distillation apparatus employed in one, some or all of those steps may be configured such that all or some of its components which, in use of the distillation apparatus, would come into contact with the distillate or process fluid, are produced from fluoropolymers, fluorochloropolymers, glass, enamel, phenolic resin impregnated graphite, silicium carbide and/or fluoropolymer impregnated graphite.

Advantageously, the use of a chlorinated alkane starting material with very low metal content and distillation apparatus which is free of metallic components that contact the working fluid during use lead to improved conversion to the target products and with reduced loss to side products.

In embodiments of the process of the invention, the distillation technique/apparatus employed may enable multiple streams to be extracted from the reaction mixture. For example, multiple streams of the isomers of interest may be extracted from the reaction mixture, where those isomers have a wide range of boiling points. These streams or fractions can then be blended to form the reaction mixture comprising a plurality of $C_3$ chlorinated alkane isomers, optionally at a desired ratio of the isomers.

The inventors have determined that, under certain operating conditions, the presence of dissolved or entrained chlorine in the reaction mixture comprising $C_3$ chlorinated alkane isomers may result in the formation of unwanted impurities in downstream reactions in which those isomers (or compounds formed therefrom) are employed. Thus, in embodiments of the invention, reaction mixture comprising a plurality of $C_3$ chlorinated alkane isomers extracted from the chlorination zone or obtained as a $C_3$ chlorinated alkane isomer rich stream upon distillation may comprise less than about 0.1%, less than about 0.05% or less than about 0.01% chlorine. The control of the chlorine content in these mixtures can be achieved using any technique known to those skilled in the art. For example, the chlorine content can be controlled through the careful control of the amount of chlorine supplied to the chlorination zone or by control of the ratio of chlorinated alkane starting material:chlorinated alkane product isomers in the chlorination zone. As discussed herein, the careful control of the amount of chlorine supplied to the chlorination zone advantageously also enables the rate of conversion of the $C_3$ chlorinated alkane starting material to be controlled.

The inventors have also found that, under certain operating conditions, the exposure of the reactants used in the processes of the present invention as well as the compounds formed in those processes to sources of oxygen and/or moisture, including air, water vapour and/or water can lead to the formation of unwanted impurities. Thus, in embodiments of the present invention, chlorination and/or distillation may be conducted in the absence of oxygen.

Even where steps are taken to minimise the exposure of the reactants/products of the processes of the present invention from exposure to oxygen and/or moisture, under certain operating conditions, the formation of oxygenated organic compounds (which have been found by the inventors to be problematic in certain downstream processes in which the products of the processes of the present invention may be employed) cannot be totally prevented. Accordingly, where such compounds are present in the reaction mixture and/or a $C_3$ chlorinated alkane isomer rich stream, that mixture/stream may be processed to remove the unwanted oxygenated organic compounds therefrom.

Indeed, it will be appreciated that, regardless of how mixtures of $C_3$ chlorinated alkane isomers are produced, such a step can be employed to reduce the content of (or ideally remove) oxygenated organic compounds from those mixtures. Thus, according to a further aspect of the invention, there is provided a process for purifying a mixture comprising at least two $C_3$ chlorinated alkane isomers and one or more oxygenated organic compounds comprising feeding the mixture into an aqueous treatment zone, contacting the mixture with an aqueous medium and extracting a treated mixture comprising reduced levels of oxygenated compounds.

The aqueous treatment step, where conducted, may be carried out before none, one, some or all of any distillation steps that are carried out.

Advantageously, the aqueous treatment step can achieve removal of oxygenated impurities in two ways. Firstly, the aqueous medium can achieve physical process extraction of oxygenated compounds. Additionally, for some compounds, these may be converted by hydrolysis to more easily separable compounds. Propanoyl chlorides are an example of compounds which are firstly hydrolysed to form their corresponding carboxylic acids which can then be extracted to an aqueous phase.

In such embodiments, the mixture subjected to the aqueous treatment step may be reaction mixture extracted from the chlorination zone. Alternatively, the mixture may be a plurality of $C_3$ chlorinated alkane isomer stream obtained via distillation from the reaction mixture. In a further alternative arrangement, the mixture subjected to aqueous treatment may be partially distilled reaction mixture, i.e. reaction mixture extracted from the chlorination zone from which one or more of an unreacted $C_3$ chlorinated alkane starting material stream, one or more single isomer streams and/or one or more distillation residue streams has already been obtained via distillation.

In processes of the present invention in which such an aqueous treatment step is performed, the step may be repeated any number of times to obtain a treated mixture of acceptable purity. For example, the steps of contacting the mixture with an aqueous medium and extracting a treated mixture therefrom may be repeated 1, 2, 3, 4, 5, 6, 7, 8, 9 or more times. Temperatures for this treatment may range from about 0 to about 100° C. for the alkane. The corresponding batch time or mean residence time for this step may be around 0.01 to about 10 hours.

In embodiments of the invention in which an aqueous treatment step is conducted, the treated mixture may comprise oxygenated organic compounds in amounts of about 1000 ppm or less, about 500 ppm or less, about 200 ppm or less, about 100 ppm or less, about 50 ppm or less, about 20 ppm or less, about 10 ppm or less, about 5 ppm or less or about 2 ppm or less.

The treated mixture also preferably comprises a plurality of $C_3$ chlorinated alkane isomers at a purity of about 95% or higher, about 97% or higher, about 99% or higher, about 99.5% or higher, about 99.7% or higher, about 99.8% or higher or about 99.9% or higher, and further comprises:
  less than about 10000 ppm, less than about 5000 ppm, less than about 2000 ppm,
  less than about 1000 ppm, less than about 500 ppm, less than about 200 ppm, less than about 100 ppm, less than about 50 ppm, less than about 20 ppm, less than about 10 ppm or less than about 5 ppm of under chlorinated impurities,
  less than about 5000 ppm, less than about 2000 ppm, less than about 1000 ppm, less than about 500 ppm, less than about 200 ppm, less than about 100 ppm, less than about 50 ppm, less than about 20 ppm, less than about 100 ppm or less than about ppm of over chlorinated impurities,
  less than about 5000 ppm, less than about 2000 ppm, less than about 1000 ppm, less than about 500 ppm, less than about 200 ppm, less than about 100 ppm, less than about 50 ppm, less than about 20 ppm, less than about 100 ppm or less than about ppm of chlorinated alkene compounds,
  less than about 1000 ppm, less than about 500 ppm, less than about 200 ppm, less than about 100 ppm, less than about 50 ppm, less than about 20 ppm, less than about ppm or less than about 5 ppm of compounds having a different number of carbon atoms than the isomers,
  less than about 1000 ppm, less than about 500 ppm, less than about 200 ppm, less than about 100 ppm, less than about 50 ppm, less than about 20 ppm, less than about ppm less than about 5 ppm, or less than about 2 ppm of oxygenated organic impurities,
  less than about 500 ppm, less than about 200 ppm, less than about 100 ppm, less than about 50 ppm, less than about 20 ppm, less than about 10 ppm or less than about 5 ppm metal, and/or
  less than about 100 ppm, less than about 50 ppm, less than about 20 ppm, less than about 100 ppm or less than about 5 ppm water.

Examples of aqueous media which may be employed in the aqueous treatment step include water and steam. Additionally or alternatively, acid (mineral, organic, etc.) may also be added to provide a pH to the mixture in the aqueous treatment zone of about 6 or lower, about 4 or lower, or about 2 or lower.

Performance of an aqueous treatment step is preferable as this reduces the content of oxygenated organic compounds present as impurities in the composition comprising a plurality of $C_3$ chlorinated alkane isomers. Examples of oxygenated organic compounds include chlorinated alkanols, chlorinated acid chlorides, chlorinated acids, chlorinated ketones or chlorinated aldehydes.

In processes of the present invention in which an aqueous treatment step is performed, the mixture fed into the aqueous treatment zone may have a low chlorine content, for example about 0.8% or less, about 0.5% or less, about 0.1% or less, about 0.05% or less or about 0.01% or less. For the avoidance of doubt, where reference is made in this context to chlorine, this encompasses free chlorine, unreacted chlorine, and dissolved chlorine. Chlorine which is bonded to atoms other than chlorine should not be considered.

In embodiments of the invention, the aqueous treatment zone is in a washing tank, for example a washing stirred tank. In such embodiments, the mixture may be washed with water and/or steam Once the mixture has been contacted with the aqueous medium, it may be subjected to one or more treatment steps. For example, the mixture can be extracted from the aqueous treatment zone and distilled (preferably under reduced pressure and/or low temperature) to provide the treated mixture.

Additionally or alternatively, in embodiments of the invention, a biphasic mixture may be formed in the aqueous treatment zone. Separation of the phases can then occur, for example extractive separation involving the hydrolysis and extraction of undesired polar or medium-polar oxygenated compounds into the water.

In such embodiments, the phase separation step involves the organic phase containing the chlorinated alkane isomers being separated from the aqueous waste phase. This may be achieved by the sequential extraction of the phases from the aqueous treatment zone. Alternatively, the biphasic mixture could be extracted from the aqueous treatment zone and subjected to a phase separation step remote from the aqueous treatment zone.

The aqueous treatment steps can be repeated if required, for example, one, two, three or more times or periodically in an extraction column, optionally with a suitable chemical reaction.

The organic phase obtained from the aqueous treatment step may optionally be dried, e.g. using a desiccant such as calcium chloride.

As mentioned above, the main aim of the aqueous treatment step, if performed is to reduce the content of oxygenated impurities which are present in the mixture subjected to that step.

In embodiments in which a Lewis acid is employed as a catalyst in the chlorination reaction, a catalyst removal step may be performed. This may be performed as a washing step, employing some or all of the conditions, techniques and apparatus discussed below in connection with the post-dehydrochlorination washing step.

Advantageously, in embodiments in which a washing step is performed, that washing step is conducted such that it both results in extraction of the catalyst from the mixture subjected to the washing step but also serves to reduce the content of oxygenated impurities from the mixture and thus additionally has the function of an aqueous treatment step.

In embodiments of the present invention, the mixture comprising the $C_3$ chlorinated alkane isomers obtained from the chlorination step (or, if performed, the aqueous treatment step/s) is subjected to a purification step, for example a distillation step. The distillation step may be conducted using the same (or different) apparatus and conditions as employed in the post-chlorination distillation step discussed above. Thus, in embodiments of the invention, a step of distilling the treated mixture to obtain a stream comprising the plurality of $C_3$ chlorinated alkane isomers at higher purity than in the mixture fed in to the aqueous treatment zone may be conducted. The distillation may be conducted at a temperature of about 130° C. or less.

The processes outlined herein provide a plurality of $C_3$ chlorinated alkane isomers.

Those skilled in the art will recognise that chlorination of $C_3$ chlorinated alkane starting materials will, depending on the reaction conditions employed, typically and to a certain extent consistently produce the same plurality of isomers, i.e. the same compounds at broadly speaking the same ratios.

The present invention is based upon the inventors identifying the applicability of pluralities of $C_3$ chlorinated alkane isomers in downstream reactions. Such isomers have previously been seen as undesirable on the basis that the isomers of interest are provided as a component in a mixture and, in many cases, are difficult to separate from other isomers, for example on the basis of similar boiling points. Indeed, substantial effort has been made to provide such alkanes having the highest possible degree of purity.

As mentioned above, the inventors have determined that the isomer mixtures of the present invention may be employed in a range of industrially applicable and commercially viable processes.

Thus, according to a further aspect of the present invention, there is provided a process for producing a $C_3$ chlorinated alkene comprising providing a mixture comprising a plurality of $C_3$ chlorinated alkane isomers, the boiling point of at least two of the plurality of $C_3$ chlorinated alkane isomers differing by ≤about 15° C., comprising subjecting the mixture to a selective dehydrochlorination step in a dehydrochlorination zone in which one of the at least two $C_3$ chlorinated alkane isomers, a first $C_3$ chlorinated alkane isomer, is selectively converted to a respective first $C_3$ chlorinated alkene without the substantial dehydrochlorination of any of the other of the plurality of $C_3$ chlorinated alkane isomers.

Advantageously, the process of this aspect of the present invention results in the formation of a first chlorinated alkene isomer having a boiling point which is sufficiently different (typically lower) than the boiling point of the chlorinated alkane isomers. Thus, the chlorinated alkene product of interest can be efficiently and easily isolated, for example, by distillation.

The process of this aspect is advantageous as it enables $C_3$ chlorinated alkane isomers which may otherwise be difficult to separate to be dehydrochlorinated with a high degree of selectivity such that one of the chlorinated alkane isomers is converted to a corresponding alkene without the substantial conversion of any of the other alkane isomers present. By 'without substantial conversion', it is meant that less than about 5%, less than about 2%, less than about 1%, less than about 0.5%, less than about 0.2%, less than about 0.1%, less than about 0.05%, less than about 0.02% or less than about 0.01% of any of the other $C_3$ chlorinated alkane isomers present in the mixture are dehydrochlorinated to their respective alkene, by weight of the respective alkane isomer.

For the avoidance of doubt, where reference is made to first and second $C_3$ chlorinated alkane isomers present in the dehydrochlorination zone and mixtures downstream of the dehydrochlorination step, these terms are not necessarily applicable to $C_3$ chlorinated alkane isomers formed in the chlorination step discussed herein, and vice versa. For example, an isomeric pair of 1,1,1,2,3-pentachloropropane and 1,1,1,3,3-pentachloropropane could be produced in the chlorination step, with 1,1,1,2,3-pentachloropropane being referred to, within the context of that reaction and downstream processing steps (prior to dehydrochlorination), as the first isomer and 1,1,1,3,3-pentachloropropane being referred to as the second isomer. However, if that plurality of isomers is then employed in the dehydrochlorination step, then 1,1,1,3,3-pentachloropropane may be referred to as the first $C_3$ chlorinated alkane isomer, within the context of that reaction and its downstream processing steps, and 1,1,1,2,3-pentachloropropane may be referred to as the second $C_3$ chlorinated alkane isomer. Alternatively, 1,1,1,2,3-pentachloropropane may be referred to as the second $C_3$ chlorinated alkane isomer, within the context of the dehydrochlorination reaction and its downstream processing steps, and 1,1,1,3,3-pentachloropropane may be referred to as the first $C_3$ chlorinated alkane isomer.

The selective dehydrochlorination of one of the $C_3$ chlorinated alkane isomers is preferably at least about 95%, about 98%, about 99%, about 99.5% or about 99.7% selective in favour of the conversion of one isomer present in the mixture.

While U.S. Pat. No. 8,987,535 provides a process for preparing a potentially useful isomer mix, a successful treatment of this mixture to yield high grade individual compounds has not been achieved. The present inventors have developed a process for preparing a high grade mix of isomers which minimizes or ideally prevents the formation of side impurities. According to the processes of the present invention, one of those isomers can selectively be converted to its respective $C_3$ chlorinated alkene which can then be easily isolated on an industrial plant scale, in preferably continuous mode, and using common upstream feedstocks.

For ease of reference, the first $C_3$ chlorinated alkane isomer to be selectively dehydrochlorinated to yield a respective chlorinated alkene is referred to as the first $C_3$ chlorinated alkane isomer. Likewise, the alkene obtained from the dehydrochlorination step is referred to as the first $C_3$ chlorinated alkene.

As mentioned above, the mixture comprising a plurality of $C_3$ chlorinated alkane isomers may comprise any number of component isomers (i.e. isomers being present in an amount of 1% or more by weight of the total isomer mixture). However, in this aspect of the invention, at least two of the component isomers must have a boiling point which varies by ≤about 20° C. In embodiments of the invention, the boiling point of the at least two component isomers may vary by a lesser degree, e.g. by ≤about 15° C., by ≤about 10° C. or by ≤about 5° C.

While the selective conversion of one of the chlorinated alkane isomers to its respective chlorinated alkene facilitates the straightforward separation of that alkene from its chlorinated alkane, it has been found that mixtures of chlorinated alkanes and chlorinated alkenes obtainable from this aspect of the present invention are of commercial value. Examples of such specific combinations include i) 1,1,1,2,3-pentachloropropane and 1,1,2,3-tetrachloro-1-propene (HCO-1230xa), ii) 1,1,3,3-tetrachloro-1-propene (HCO-1230za) and 1,1,1,2,3-pentachloropropane (HCC-240db), iii) 1,1,3,3-tetrachloro-1-propene (HCO-1230za), 1,1,1,2,3-pentachloropropane (HCC-240db) and 1,1,2,3-tetrachloro-1-propene (HCO-1230xa), iv) 1,1,1,3,3-pentachloropropane (HCC-240fa), 1,1,3,3-tetrachloro-1-propene (HCO-1230za), and/or 1,3,3,3-tetrachloro-1-propene (HCO-1230zd).

The dehydrochlorination step of this aspect of the invention may be conducted in any phase, including the liquid or gas phase.

For the avoidance of doubt, the mixture comprising a plurality of $C_3$ chlorinated alkane isomers may be obtainable from the processes discussed herein. Additionally or alternatively, the plurality of isomers may be obtained from an alternative process for preparing such compositions.

Regardless of how the mixture comprising a plurality of $C_3$ chlorinated alkane isomers is prepared, it preferably has low levels of impurities.

For example, that mixture comprising the plurality of $C_3$ chlorinated alkane isomers preferably has a purity (i.e. a content as percentage by weight) of about 95% or higher, about 97% or higher, about 99% or higher, about 99.5% or higher, about 99.7% or higher about 99.8% or higher, or about 99.9% or higher and preferably further comprises:

less than about 10000 ppm, less than about 5000 ppm, less than about 2000 ppm, less than about 1000 ppm, less than about 500 ppm, less than about 200 ppm, less than about 100 ppm, less than about 50 ppm, less than about 20 ppm, less than about ppm or less than about 5 ppm of under chlorinated impurities, less than about 5000 ppm, less than about 2000 ppm, less than about 1000 ppm, less than about 500 ppm, less than about 200 ppm, less than about 100 ppm, less than about 50 ppm, less than about 20 ppm, less than about 100 ppm or less than about ppm of over chlorinated impurities, less than about 5000 ppm, less than about 2000 ppm, less than about 1000 ppm, less than about 500 ppm, less than about 200 ppm, less than about 100 ppm, less than about 50 ppm, less than about 20 ppm, less than about 100 ppm or less than about ppm of chlorinated alkene compounds, less than about 1000 ppm, less than about 500 ppm, less than about 200 ppm, less than about 100 ppm, less than about 50 ppm, less than about 20 ppm, less than about ppm or less than about 5 ppm of compounds having a different number of carbon atoms than the isomers, less than about 1000 ppm, less than about 500 ppm, less than about 200 ppm, less than about 100 ppm, less than about 50 ppm, less than about 20 ppm, less than about 100 ppm less than about 5 ppm, or less than about 2 ppm of oxygenated organic impurities, less than about 500 ppm, less than about 200 ppm, less than about 100 ppm, less than about 50 ppm, less than about 20 ppm, less than about 100 ppm or less than about 5 ppm metal, and/or less than about 100 ppm, less than about 50 ppm, less than about 20 ppm, less than about 100 ppm or less than about 5 ppm water.

In embodiments of this process of the invention, the mixture which is subjected to selective dehydrochlorination may comprise a first and a second isomer present in a molar ratio of about 95:5, about 90:10, about 80:20, about 70:30, about 60:40, about 50:50, about 40:60, about 30:70, about 20:80, about 10:90 or about 5:95 to about 5:95, about 10:90, about 20:80, about 30:70, about 40:60, about 50:50, about 60:40, about 70:30, about 80:20, about 90:10 or about 95:5.

In embodiments of the invention, one, two, or all of the chlorinated alkane isomers formed in the chlorination zone are compounds having a trichlorinated terminal carbon atom.

The plurality of isomers in the mixture may be i) 1,1,1,3,3-pentachloropropane and 1,1,1,2,3-pentachloropropane, ii) 1,1,1,2,3-pentachloropropane and 1,1,2,2,3-pentachloropropane, or iii) 1,1,2,2,3-pentachloropropane and 1,1,1,2,2-pentachloropropane. In the isomeric pairs outlined in this paragraph, the first listed isomer may be the first $C_3$ chlorinated alkane isomer or the second $C_3$ chlorinated alkane isomer, and the second listed isomer may be the other of the first $C_3$ chlorinated alkane isomer or the second $C_3$ chlorinated alkane isomer.

Thus, according to a further aspect of the present invention, the use of a mixture comprising a plurality of $C_3$ chlorinated alkane isomers in a dehydrochlorination step is provided, wherein the mixture has a purity (i.e. a content as percentage by weight) of about 95% or higher, about 97% or higher, about 99% or higher, about 99.5% or higher, about 99.7% or higher about 99.8% or higher, or about 99.9% or higher of the plurality of $C_3$ chlorinated alkane isomers and preferably further comprises:

less than about 10000 ppm, less than about 5000 ppm, less than about 2000 ppm, less than about 1000 ppm, less than about 500 ppm, less than about 200 ppm, less than about 100 ppm, less than about 50 ppm, less than about 20 ppm, less than about ppm or less than about 5 ppm of under chlorinated impurities, less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about ppm of over chlorinated impurities, less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about ppm of chlorinated alkene compounds, less than about 1000 ppm, less than about 500 ppm, less than about 200 ppm, less than about 100 ppm, less than about 50 ppm, less than about 20 ppm, less than about ppm or less than about 5 ppm of compounds having a different number of carbon atoms than the isomers, less than about 1000 ppm, less than about 500 ppm, less than about 200 ppm, less than about 100 ppm, less than about 50 ppm, less than about 20 ppm, less than about ppm less than about 5 ppm, or less than about 2 ppm of oxygenated organic impurities, less than about 500 ppm, less than about 200 ppm, less than about 100 ppm, less than about 50 ppm, less than about 20 ppm, less than about 10 ppm or less than about 5 ppm metal, and/or less than about 100 ppm, less than about 50 ppm, less than about 20 ppm, less than about 10 ppm or less than about 5 ppm water.

The mixture comprising the plurality of $C_3$ chlorinated alkane isomers employed in this aspect of the present invention may additionally comprise any property of mixtures used as starting materials for dehydrochlorination reactions described herein in connection with other aspects of the invention.

Those skilled in the art will be familiar with techniques and apparatus that may be employed in dehydrochlorination reactions. Such processes may be employed in the process of this aspect of the present invention provided that they enable the selective dehydrochlorination of a first $C_3$ chlorinated alkane isomer without the substantial conversion of any of the other isomers present in the mixture. While dehydrochlorination techniques and apparatus were known, the use of such processes to selectively dehydrochlorinate one isomer from a plurality of isomers has not previously been conducted and is not intuitive. Operating a process in this way enables the successful and efficient recovery of high grade individual products.

It has been found that alkaline dehydrochlorination as employed in the prior art may not be industrially feasible in the processes of the present invention as a result of economic and environmental drawbacks. Further, a substantial amount of carbonyl compounds (found to be particularly problematic in downstream processes by the inventors) are formed during alkaline hydroxide dehydrochlorination. Additionally, the presence of alkaline agents in dehydrochlorination to form certain alkenes (e.g. 1,1,3,3-tetrachloropropene) can result in the formation of explosive mixtures. In tests performed by the inventors, it was found that alkaline dehydrochlorination of the mixture of 1,1,1,3,3-pentachloropropane and 1,1,1,2,3-pentachloropropane (80:20 ratio), does not give the required selectivity towards one chlorinated alkene; both 1,1,3,3-tetrachloropropene and 2,3,3,3-tetrachloropropene are produced.

Particularly preferred dehydrochlorination processes are disclosed in WO2016/0580567, the contents of which are incorporated by reference.

The reaction mixture is maintained in the dehydrochlorination zone for a period sufficient to enable the reaction (the conversion of first $C_3$ chlorinated alkane to the first $C_3$ chlorinated alkene) to proceed to the required degree of completion. In embodiments of the invention, in which dehydrochlorination occurs in the liquid phase, the residence time of the reaction mixture in the dehydrochlorination zone may range from about 0.1, about 0.2, about 0.5, about 1, about 1.5, about 2, about 2.5 or about 3 to about 5 hours, about 7 hours, about 9 hours or about 10 hours.

In embodiments in which dehydrochlorination is conducted in the liquid phase, the operating temperature of the dehydrochlorination zone may be in the range of about 50° C., about 70° C., about 100° C. or about 120° C. to about 150° C., about 170° C., about 200° C. or about 250° C.

The dehydrochlorination zone may be operated at subatmospheric pressure, atmospheric pressure or superatmospheric pressure. In embodiments of the invention, the dehydrochlorination zone is operated at atmospheric pressure, or at a pressure of about kPa to about 400 kPa, about 40 kPa to about 200 kPa, or about 70 kPa to about 150 kPa.

Any catalyst which increases the rate of the dehydrochlorination reaction may be employed in the processes of the present invention. In embodiments, the catalyst comprises a metal. In such embodiments, the metal may be present in solid form (e.g. where the catalyst is iron, it may be present as particulate iron (e.g. iron filings or iron powder) iron mesh, iron wire, packing (structured or random), fixed bed, fluid bed, dispersions in liquid, etc. or in alloys containing iron formed in any such way, e.g. carbon steel), and/or as a salt (e.g. where the catalyst is iron, it may be present as ferric chloride, ferrous chloride, etc.). Additionally or alternatively, the apparatus in which the process of the present invention is conducted may be provided with components formed either partially or totally of catalyst material, for example column internals.

In embodiments of the invention in which metal is present in the reaction mixture as a salt, it may be added to the reaction mixture in salt form and/or solid metal may be added to the reaction mixture, which then dissolves in the reaction mixture, forming the salt in situ. When present in the form of a salt, the catalyst may be added in an amorphous form, crystalline form, an anhydrous form and/or in hydrated form (e.g. ferric chloride hexahydrate). Liquid form catalysts may also be employed.

Examples of catalysts which may be employed in the dehydrochlorination step/s include one or more halides (e.g. chlorides, bromides, fluorides or iodides) of transition metals such as iron, aluminium, antimony, lanthanum, tin, titanium. Specific examples of catalysts that may be employed include $FeCl_3$, $AlCl_3$, $SbCl_5$, $SnCl_4$, $TiCl_4$.

In embodiments of the invention, the mixture comprises 1,1,1,3,3-pentachloropropane and 1,1,1,2,3-pentachloropropane as the plurality of isomers, preferably in a molar ratio of 80:20, 90:10, 93:7, or 95:5. The mixture is subjected to selective dehydrochlorination such that 1,1,3,3-tetrachloropropene (HCO-1230za) is produced selectively in preference to 1,1,2,3-tetrachloropropene (HCO-1230xa), leaving 1,1,1,2,3-pentachloropropane largely unconverted. The obtained chlorinated alkene, 1,1,3,3-tetrachloropropene (HCO-1230za) can be easily separated from the mixture. The residual mixture, rich in 1,1,1,2,3-pentachloropropane can be subjected to treatment steps.

The feed of the mixture comprising $C_3$ chlorinated alkane isomers and/or catalyst into the dehydrochlorination zone may be continuous or intermittent, as may extraction of the reaction mixture. In embodiments, the continuous mode is preferred.

One advantage of the processes of the present invention is that desirous results are obtained whether the dehydrochlorination zone is operated in a continuous or batch process. The terms 'continuous process' and 'batch process' will be understood by those skilled in the art. In embodiments, the continuous mode is preferred.

A further advantage of the present invention is that it enables high purity chlorinated alkene compounds to be produced without the use of alkaline hydroxides. This is advantageous as the avoidance of the use of alkaline hydroxide means that the formation of carbonyl compounds can be reduced or eliminated. Additionally, and unexpectedly, the present inventors have found that alkaline hydroxide-free dehydrochlorination steps are more selective than if alkaline hydroxide is employed. Further, the risk of formation of potentially explosive mixtures of chlorinated alkenes and alkaline agents can be minimised.

Thus, in embodiments of the present invention, no alkaline hydroxide is added to the dehydrochlorination zone and/or the reaction mixture present in the dehydrochlorination zone is free of alkaline hydroxide.

It will be recognised that, as the reaction proceeds, the first $C_3$ chlorinated alkene will be produced in the dehydrochlorination zone. In embodiments of the invention, the first $C_3$ chlorinated alkene is extracted from the dehydrochlorination zone (either directly, or by firstly extracting reaction mixture from the dehydrochlorination zone and then extracting the first $C_3$ chlorinated alkene therefrom, for example via distillation). This extraction may be conducted continuously or intermittently.

For the avoidance of doubt, where reference is made to 'continuous extraction' from the reaction mixture or directly from the dehydrochlorination zone, a strict literal interpretation is not intended; one skilled in the art would recognise that the term is used to mean that extraction (of the reaction mixture from the dehydrochlorination zone or via direct extraction of the first $C_3$ chlorinated alkene, e.g. via distillation) occurs on a substantially continuous basis, once the dehydrochlorination zone has attained the target operating conditions and the reaction mixture has attained a steady state.

Additionally or alternatively, the first $C_3$ chlorinated alkene can be extracted directly from the reaction mixture in the dehydrochlorination zone (e.g. via direct distillation), and/or a portion of the reaction mixture can firstly be extracted from the dehydrochlorination zone and the chlorinated alkene then subsequently extracted from that mixture, remotely from the dehydrochlorination zone. In embodiments where reaction mixture is extracted from the dehydrochlorination zone, one or more treatment steps (e.g. a washing step, discussed below) may be carried out prior to and/or following distillation.

In embodiments of the invention, the first $C_3$ chlorinated alkene may be removed from the reaction mixture by distillation. Any technique and apparatus known to those skilled in the art may be employed to effect extraction of the first $C_3$ chlorinated alkene from the reaction mixture in this way. In embodiments of the invention, a distillation column may be used, for example a rectification column. The reaction mixture may pass (in the case of direct distillation) or be fed into the column bottom following extraction of the reaction mixture from the dehydrochlorination zone, with the first $C_3$ chlorinated alkene of interest being removed from the top of the column as a liquid distillate.

For example, in 'direct distillation' embodiments, in which the reaction mixture is totally or partially gaseous, for example due to the operating temperature in the dehydrochlorination zone, the apparatus may be configured such that the dehydrochlorination zone is in fluid communication with the distillation apparatus. In such embodiments, the distillation apparatus may be coupled to the dehydrochlorination zone. Conveniently, this enables the gaseous first $C_3$ chlorinated alkene-containing mixture to pass (or be passed) directly from the dehydrochlorination zone in to the distillation apparatus. Alternatively, the distillation apparatus may be located remotely from the dehydrochlorination zone, meaning that the gaseous mixture must be extracted from the dehydrochlorination zone and passed to the distillation apparatus.

Additionally or alternatively, where the reaction mixture is present in the dehydrochlorination zone either partly or totally in liquid form, a portion of the liquid reaction mixture may be extracted from the dehydrochlorination zone and passed to distillation apparatus. In such embodiments, the reaction mixture may be subjected to one or more treatment steps (e.g. a washing step, discussed below) which precede and/or follow distillation.

In embodiments in which the first $C_3$ chlorinated alkene is extracted from the reaction mixture by distillation, at least about 50%, at least about 60%, at least about 70%, at least about 80%, or at least about 90% by weight of the first $C_3$ chlorinated alkene present in the reaction mixture subjected to distillation is extracted from that mixture.

Distillation of the first $C_3$ chlorinated alkene from the reaction mixture can be carried out continuously, semi-continuously or batch-wise.

A further advantage of the present invention is that the dehydrochlorination reaction produces highly pure gaseous hydrogen chloride from the chlorinated alkene mixture that can be recovered using routine techniques, for example by condensation of overhead vapours.

Thus, in embodiments of the invention in which hydrogen chloride is produced during the dehydrochlorination reaction, the hydrogen chloride may be extracted. This can be achieved using any equipment and/or techniques for doing so known to those skilled in the art. For example, if the reaction mixture is subjected to distillation, the distillation apparatus may be provided—with a condenser (e.g. a partial condenser), or a condenser (e.g. a partial condenser) may be provided downstream of the reactor apparatus, to enable the removal of hydrogen chloride gas.

In embodiments of the present invention, in which hydrogen chloride gas is extracted from the dehydrochlorination zone or from reaction mixture extracted therefrom, this may be achieved through the use of deep cooling, i.e. by extracting the gas from the reaction mixture and then cooling it to a temperature of about 0° C. or lower, about −10° C. or lower or about −20° C. or lower.

Cooling apparatus (e.g. a second condenser) may additionally be employed, e.g. downstream of the first condenser. Arranging the apparatus in this way is advantageous as the first condenser can be used to condense the bulk of the chlorinated alkene, with the second condenser being used to purify the gas by condensing traces of the chlorinated alkene.

The resulting condensate may be recycled back to the dehydrochlorination zone or optionally used in other associated reaction zones.

Optionally, in order to produce very pure hydrogen chloride gas, a crude hydrogen chloride gas after the first partial condensation together with remaining traces of chlorinated alkene isomer can be subjected a chlorination step, preferably by means of UV light, in order to produce heavier chlorinated molecules, which can be easily condensed in the second partial condensation and thus separated completely from HCl gas. The resulting condensate containing such heavy chlorinated molecules, may be further processed or treated e.g. in high temperature chlorinolysis plant or in incineration plant.

Additionally or alternatively, an active carbon adsorption column may be employed to adsorb traces of chlorinated alkene from hydrogen chloride gas.

Additionally or alternatively, an absorption column may be employed to absorb hydrogen chloride gas to produce hydrochloric acid solution.

Thus, advantageously, hydrogen chloride extracted as discussed herein is highly pure and thus can be used as a reactant in upstream or downstream reactions in the same industrial plant. An example of downstream use is for the hydrochlorination of glycerol to make monochlorohydrin and/or dichlorohydrin, and subsequently to lead to epichlorohydrin, glycidol and epoxies.

In embodiments of the invention, the extraction of high grade first $C_3$ chlorinated alkene from the dehydrochlorination zone may be achieved by direct distillation. Additionally or alternatively, reaction mixture may firstly be extracted from the dehydrochlorination zone and then (possibly following one or more treatment steps, such as a washing step, discussed below) subjected to distillation to extract high grade first $C_3$ chlorinated alkene. Any distillation apparatus or techniques effective to extract the first $C_3$ chlorinated alkene from the dehydrochlorination zone (or reaction mixture extracted from that zone) may be employed.

It has been found by the inventors that, under certain operating conditions, controlling the mixture within the dehydrochlorination zone such that the first $C_3$ chlorinated alkane isomer does not achieve total conversion to respective first $C_3$ chlorinated alkene can prevent the inadvertent and unwanted dehydrochlorination of other $C_3$ chlorinated alkane isomers present. Thus, in embodiments of the invention, the reaction conditions in the dehydrochlorination zone are controlled such that the total conversion of the first $C_3$ chlorinated alkane isomer does not occur. In such embodiments, the degree of conversion of the first $C_3$ chlorinated alkane isomer to its respective first $C_3$ chlorinated alkene is prevented from exceeding about 95%, about 90%, about 80%, about 75% or about 70%.

The degree of conversion of the first $C_3$ chlorinated alkane isomer to its respective first $C_3$ chlorinated alkene may be controlled in one or more of the following ways: i) control of the operating conditions in the dehydrochlorination zone (e.g. temperature, pressure, agitation speed, residence time etc. which do not favour higher levels of chlorinated alkene formation, and/or ii) by controlling the amount of chlorinated alkane starting material and/or catalyst present in the dehydrochlorination zone. Control of the amount of chlorinated alkane isomer mixture starting material can be achieved through control of the feed rate of the starting material into the dehydrochlorination zone.

In embodiments of the invention, residual mixture comprising the first $C_3$ chlorinated alkane isomer, one or more additional chlorinated alkane isomers, optionally the first $C_3$ chlorinated alkene, and optionally catalyst may be extracted from the dehydrochlorination zone and/or distillation apparatus. The molar ratio of the first $C_3$ chlorinated alkane isomer:one or more additional chlorinated alkane isomers present in the reaction mixture extracted from the dehydrochlorination zone may be in the region of 10:1, 7:1 or 5:1 to about 4:1, 3:1, 2:1, about 1:1 or about 0.5:1.

The mixture extracted from the dehydrochlorination zone and/or distillation apparatus can then be subjected to additional treatment steps. In other words, the washing step may be carried out prior to or following any distillation step that is carried out to extract the stream rich in or consisting of the first $C_3$ chlorinated alkene.

For example, the residual mixture can be subjected to a washing step. In such a step, the residual mixture is contacted with an aqueous medium in an aqueous treatment zone which serves to deactivate the catalyst (if present). The residual mixture may also optionally be contacted with acid in the aqueous treatment zone, for example inorganic acid such as sulphuric acid, phosphoric acid and/or hydrochloric acid. The acid may be pure, or may be dilute. The aqueous treatment step has the advantageous effect of removing certain classes of otherwise problematic impurities from the residue, especially oxygenated impurities.

In such embodiments, catalyst deactivation can be achieved with only a short contact time, e.g. about 5, about 10, about 20 or about 30 minutes, with water at low temperature is required. For hydrolysis and extraction of chlorinated, oxygenated impurities, the contact time with the water is longer, e.g. up to about 1 hour, about 2 hours, about 5 hours or about 10 hours and/or at a temperature of about 50° C. or less, about 40° C. or less or about 30° C. or less.

Where a dilute acid is employed, this may additionally provide the aqueous medium with which the residual mixture is contacted. Additionally, or alternatively, the aqueous medium may comprise water (in any form, e.g. including steam) which may be added separately into the aqueous treatment zone.

In embodiments in which acid is added into the aqueous treatment zone, this preferably reduces the pH of the mixture present therein to about 5 or lower, about 4 or lower, about 2 or lower or about 1 or lower.

Contacting the residual mixture (which comprises the first $C_3$ chlorinated alkane isomer, one or more additional chlorinated alkane isomers, optionally the first $C_3$ chlorinated alkene, and optionally catalyst with an aqueous medium forms a biphasic mixture.

The biphasic mixture, comprising an aqueous phase and an organic phase may be formed in the aqueous treatment zone (or in certain embodiments, remotely therefrom), as a result of the presence of both the aqueous medium and also the predominantly organic residue.

In such embodiments where a biphasic mixture is formed, the organic phase may be extracted from the biphasic mixture using phase separation techniques and/or equipment known to those skilled in the art. Where the biphasic mixture is formed in the aqueous treatment zone, the organic phase can be separated from the aqueous phase by the sequential extraction of the phases from the aqueous treatment zone. The aqueous phase, which contains impurities removed from the residue can be further treated.

To maximise phase separation efficiency and thus facilitate extraction of that phase from the biphasic mixture, a haloalkane extraction agent and/or phase separation intensifier (for example, one, some or all of the $C_3$ chlorinated alkane isomers, and/or various alcohols and/or ketones) may be added to the aqueous treatment zone, either intermittently or continuously, using techniques and/or equipment known to those skilled in the art. The use of $C_3$ chlorinated alkane isomers is preferred as these compounds are part of the product processes and do not require removal using specific separation steps. Optionally, phase separation intensifiers such as polar alcohols and/or ketones with boiling points sufficiently different to the chlorinated alkene and chlorinated alkane present in the reaction mixture may be employed. The difference in boiling points should be at least 20° C., at least about 30° C., at least about 40° C., at least about 50° C. or at least about 60° C. Examples of phase separation intensifiers that may be employed include aliphatic ketones e.g. acetone and aliphatic alcohols e.g. methanol, ethanol, propanol/s, butanol/s.

In embodiments of the invention, the extracted organic phase may then be subjected to a distillation step in which streams or fractions of the first $C_3$ chlorinated alkene (now highly purified) and, separately, $C_3$ chlorinated alkane isomers are distilled off. A heavy ends residue may be extracted from the distillation apparatus, optionally filtered and incinerated and/or subjected to high temperature chlorinolysis. A specific embodiment in which such a process is operated is presented in Example 7.

The other chlorinated alkane isomers are thus separated from the first chlorinated alkane isomer, and after distillation, may be used as such or converted to the corresponding chlorinated alkene, using the dehydrochlorination method disclosed herein or, for example, described in WO2016/058567.

To increase the stability of chlorinated alkenes produced according to the processes of the present invention, stabilising compounds can be added. This is particularly appropriate where the compounds are to be stored or transported in oxygen-containing environments. Examples of stabilisers include hydroxyl derivatives of aromatics, amines, thiazines and the like. Where employed, stabilisers may be present in amounts of about 1 to 100 ppm or about 2 to about 50 ppm.

Reducing the water content of chlorinated alkene has been found to aid stability. Thus, in embodiments of the present invention, reaction conditions are controlled such that the obtained chlorinated alkene product/s comprise less than about 100 ppm, less than about 50 ppm, or less than about 10 ppm water.

In embodiments of the present invention, the dehydrochlorination reaction is carried out in the vapour phase, i.e. both the first $C_3$ chlorinated alkane and the first $C_3$ chlorinated alkene are in gaseous form. In such embodiments, the dehydrochlorination zone may be operated at a temperature of about 250° C. to about 500° C., about 300° to about 425° C. or about 350° C. to about 400° C.

The dehydrochlorination zone may be operated at subatmospheric pressure, atmospheric pressure or superatmospheric pressure.

In embodiments of the invention in which the dehydrochlorination reaction occurs in the vapour phase, the residence time of the reaction mixture in the dehydrochlorination zone may range from about 0.5 to about 10 seconds. Additionally or alternatively, a metallic catalyst may be used, for example one containing iron at levels of 50% by weight or greater. Examples of catalysts which may be employed in processes of the present invention include stainless steels, for example ferritic and/or austenic steels. Catalysts employed in processes of the present invention preferably have an iron content of at least about 50%, at least about 60%, at least about 70%, at least about 80%, at least about 90% or at least about 95% by weight. Pure iron may be employed as a catalyst.

Catalysts may be employed in any form, for example fluid bed arrangements and/or fixed bed arrangements. Additionally or alternatively, components of the dehydrochlorination zone comprising the catalyst can be employed.

In embodiments in which the dehydrochlorination step is conducted in the vapour-phase, the reaction mixture extracted from the dehydrochlorination zone is typically in the vapour phase. Those hot product gases may be condensed using any technique and/or equipment known to those skilled in the art, to obtain chlorinated organic compounds in liquid form.

Regardless of whether dehydrochlorination is carried out in the liquid or vapour phase, the mixture of chlorinated organics, including the first $C_3$ chlorinated alkene and unreacted chlorinated alkane isomers, as well as impurities may then be subjected to one or more post-dehydrochlorination treatment steps as discussed above (including distillation and/or hydrolysis steps) to obtain the purified first $C_3$ chlorinated alkene.

Any type of reactor known to those skilled in the art may be employed in the processes of the present invention. Specific examples of reactors that may be used to provide a dehydrochlorination zone are column reactors, tubular reactors, bubble column reactions, plug-flow reactors and continuously stirred tank reactors.

The process of the present invention may be carried out in a single dehydrochlorination zone or in a plurality of dehydrochlorination zones. Where a plurality of dehydrochlorination zones are employed (for example, 2, 3, 4, 5, 6 or more dehydrochlorination zones), these may be operated in sequence (i.e. such that reaction mixture is passed along a number of dehydrochlorination zones) and/or in parallel.

In embodiments of the invention, where a plurality of dehydrochlorination zones are employed, optionally in a cascade mode, these may be in the same or different reactors. For example, where a plurality of dehydrochlorination zones are employed, these may be provided in a plurality (e.g. 1, 2, 3, 4, 5 or more) of reactors (e.g. continuously stirred tank reactors) which may each be configured to have optimized operating conditions (e.g. temperature, residence times, etc.).

In an embodiment, a plurality of dehydrochlorination zones may be present in a distillation column that may be employed in processes of the present invention. In such embodiments, dehydrochlorination may be achieved by reactive distillation, for example where the dehydrochlorination reaction is carried out on trays in a distillation column and/or on packing provided in the column. In embodiments in which reactive distillation is carried out, the distillation column preferably comprises a stripping zone in which alkene is separated from alkane. The stripping zone may be located below the liquid feed.

It has been found that the components of the reaction mixture (e.g. chlorinated alkenes, hydrogen chloride and/or the $C_3$ chlorinated alkane isomer starting materials) obtainable from the dehydrochlorination reaction which is conducted in the processes of the present invention, can unfavourably interact with certain materials. Thus, in embodiments of the invention, those parts of the dehydrochlorination zone which are in contact with the reaction mixture may have an iron content of about 20% or less, about 10% or less or about 5% or less, and/or are formed from non-metallic materials, for example enamel, glass, impregnated graphite (e.g. impregnated with phenolic resin), silicon carbide and/or plastics materials such as polytetrafluoroethylene, perfluoroalkoxy and/or polyvinylidene fluoride.

In embodiments of the invention, the surfaces of all equipment employed in the processes of the present invention with which chlorinated alkene will come into contact are formed from suitable materials such as those identified above. One possible exception is where one or more regions of the surfaces of the apparatus employed in the processes of the present invention are formed of metallic material which is selected to perform as a catalyst.

One advantage of the process of the present invention is that desirous results are obtained whether the chlorination and/or dehydrochlorination zones are operated in a continuous (steady state) or batchwise process. The terms 'continuous process' and 'batchwise process' will be understood by those skilled in the art.

As can be seen from the disclosure provided herein, the inventive processes of the present invention can be operated in an integrated process in a fully continuous mode, optionally in combination with other processes. The process steps of the present invention may employ starting compounds which are converted to highly pure intermediates which are themselves further processed to the required target chlorinated compounds having predetermined ratios to maximize their commercial value. Those compounds have the requisite purity to be employed as feedstocks in a range of downstream processes, for example hydrofluorination conversions.

The processes of the present invention enable product purity levels to be controlled to attain highly pure target compounds. The processes advantageously balance high yields, high selectivity and high efficiency which is particularly challenging, especially in continuous processes. The processes of the present invention enable high purity chlorinated alkene compounds to be economically produced on an industrial scale, those compounds having very low levels of a range of impurities.

As will be appreciated from the disclosure herein, use of the inventive chlorination and dehydrochlorination steps discussed provide efficient streamlined process for producing highly pure, commercially valuable $C_3$ chlorinated compounds. While both of those steps are independently inventive, particularly advantageous results are observed when the steps are operated in sequence.

Thus, according to a further aspect of the present invention, there is provided a process comprising:

preparing a reaction mixture comprising a plurality of $C_3$ chlorinated alkane isomers comprising chlorinating a $C_3$ chlorinated alkane starting material in a chlorination zone to produce the plurality of $C_3$ chlorinated alkane isomers, the plurality of $C_3$ chlorinated alkane isomers each having at least one more chlorine atom than the $C_3$ chlorinated alkane starting material, wherein the concentration of the $C_3$ chlorinated alkane starting material is controlled such that the molar ratio of the $C_3$ chlorinated alkane starting material:$C_3$ chlorinated alkane isomers obtained by the chlorination of the $C_3$ chlorinated starting material in the reaction mixture present in the chlorination zone does not exceed about 40:60 (i.e. conversion of the $C_3$ chlorinated alkane starting material does not exceed 60%);

subjecting the reaction mixture to one or more first distillation steps to produce a $C_3$ chlorinated alkane starting material stream, a plurality of $C_3$ chlorinated alkane isomers stream and optionally a single $C_3$ chlorinated alkane isomer stream;

subjecting the plurality of $C_3$ chlorinated alkane isomers stream to a selective dehydrochlorination step in which one of the $C_3$ chlorinated alkane isomers, the first $C_3$ chlorinated alkane isomer, is converted to a respective first $C_3$ chlorinated alkene without the substantial dehydrochlorination of any of the other of the plurality of $C_3$ chlorinated alkane isomers, and separating the first $C_3$ chlorinated alkene from the mixture prepared in the dehydrochlorination step.

For the avoidance of doubt, the chlorination, distillation, dehydrochlorination and separation steps employed in this aspect of the present invention may be operated using conditions, apparatus, reagents, catalysts, etc. as presented in connection with analogous steps herein.

In embodiments of this aspect of the present invention, no additional distillation step aside from that recited above is performed following the chlorination step and prior to the dehydrochlorination step.

Separation of the first $C_3$ chlorinated alkene is preferably achieved using distillation techniques, for example those as discussed herein.

As an example of a process of this aspect of the invention, a mixture of 1,1,1,3,3-pentachloropropane and 1,1,1,2,3-pentachloropropane may be produced with high levels of purity by chlorinating 1,1,1,3-tetrachloropropane. The mixture is then distilled to provide:

a mixture of 1,1,1,3,3-pentachloropropane and 1,1,1,2,3-pentachloropropane with a higher ratio of 1,1,1,3,3-pentachloropropane:1,1,1,2,3-pentachloropropane than in the reaction mixture present in the chlorination zone, a stream of unreacted 1,1,1,3-tetrachloropropane starting material, which can be recycled back to the chlorination zone.

pure 1,1,1,2,3-pentachloropropane which is useful in the production of downstream chlorinated alkenes and/or fluorocarbons, and heavy ends to be further treated for example by high temperature chlorinolysis or incineration.

The mixture of pentachloropropane isomers with the increased ratio 1,1,1,3,3-pentachloropropane and 1,1,1,2,3-pentachloropropane (e.g. 93:7) may then be selectively dehydrochlorinated under conditions such that only the 1,1,1,3,3-pentachloropropane is converted to its corresponding alkene, 1,1,3,3-tetrachloro-1-propene, in the presence of 1,1,1,2,3-pentachloropropane.

This mixture of 1,1,3,3-tetrachloro-1-propene and 1,1,1,2,3-pentachloropropane (with low levels of unconverted 1,1,1,3,3-pentachloropropane) is successfully, and more easily, separated by distillation to provide high purity 1,1,3,3-tetrachloro-1-propene (1230za) and a mixture of unconverted 1,1,1,3,3-pentachloropropane and 1,1,2,3-pentachloropropane, which can then be recycled to the post-chlorination distillation step or alternatively to chlorination step. The isolated 1230za can then be used as a feedstock for producing the 1-chloro-3,3,3-trifluoropropene blowing agent.

The processes of the present invention are particularly advantageous as they enable highly pure chlorinated alkane isomer mixes and alkenes to be produced using simple and straightforward techniques and equipment with which one skilled in the art would be familiar.

Examples of highly pure compounds with controlled impurity profiles that can be prepared according to the integrated, streamlined and optionally continuous processes of the present invention (from ethylene and without the use of toxic vinyl chloride) include: 1,1,3,3-tetrachloropropene, which is useful for the production of blowing agents 1233zd 1,1,1,2,3-pentachloropropane which is useful for conversion to highly pure 1230xa or for 1234yf synthesis.

As those skilled in the art will appreciate, previous methods for producing a $C_3$ plurality of chlorinated alkanes and alkenes involve several separate steps and require the use of a wider range of starting feedstocks. There would be variability in production of above desired chlorinated products. In contrast, the processes of the present invention can achieve the production of a range of commercially valuable products from a single production line using the minimum number of starting materials. Further, the processes advantageously provide raw materials that are capable for use, without extensive treatment in the following processes:

- a chlorinolysis process, utilising heavy by products from the distillation residue stream obtainable from the post-chlorination distillation step discussed above to produce the useful starting feedstock carbon tetrachloride CTC,
- the production of chlorinated alkenes from the single isomer stream obtainable from the post-chlorination distillation step discussed above a $C_3$ chlorinated feedstock process producing 1,1,1,2,3-pentachloropropane, 1,1,3,3-tetrachloropropene and 1,1,2,3-tetrachloropropene, and
- the utilisation of the hydrogen chloride gas in downstream processes, e.g. HCl electrolysis, oxychlorination, the production of dichloropropanol from glycerol, epichlorohydrin from glycerol, and pure hydrochloric acid.

In embodiments of the invention, the processes of the invention can be used to produce high purity chlorinated alkane compositions, e.g. 1,1,1,2,3-pentachloropropane. Thus, according to a further aspect of the present invention, there is provided a composition comprising a $C_3$ chlorinated alkane compound obtainable from the processes discussed herein which comprises:

The $C_3$ chlorinated alkane in amounts of at least about 95%, at least about 99.5%, at least about 99.7%, at least about 99.8%, at least about 99.9%, or at least about 99.95%, and one or more of the following:
Oxygenated organic compounds in amounts of less than about 500 ppm, about 250 ppm or less, about 100 ppm or less, about 50 ppm or less, or about 10 ppm or less,
Isomers of the chlorinated alkane of interest in amounts of less than about 500 ppm, about 250 ppm or less, or about 100 ppm or less,
Non-isomeric alkane impurities in amounts of less than about 500 ppm, about 250 ppm or less, or about 100 ppm or less,
Chlorinated alkenes in amounts of less than about 500 ppm, about 250 ppm or less, about 100 ppm or less, or about 50 ppm or less,
Water in amounts of less than about 500 ppm, about 250 ppm or less, about 100 ppm or less or about 50 ppm or less,
Inorganic compounds of chlorine in amounts of about 100 ppm or less, about 50 ppm or less, about 20 ppm or less or about 10 ppm or less,
Brominated organic compounds in amounts of about 100 ppm or less, about 50 ppm or less, about 20 ppm or less or about 10 ppm or less, and/or
Iron in amounts of about 100 ppm or less, about 50 ppm or less, about 20 ppm or less, about 10 ppm or less or about 5 ppm or less.

In embodiments of the invention, the processes of the invention can be used to produce high purity chlorinated alkene compositions, e.g. 1,1,3,3-tetrachloropropene, 2,3,3,3-tetrachloropropene, 1,1,2,3-tetrachloropropene or 1,3,3,3-tetrachloropropene. Thus, according to a further aspect of the present invention, there is provided a composition comprising a $C_3$ chlorinated alkene obtainable from the processes discussed herein which comprises:

about 95% or more, about 97% or more, about 99% or more, about 99.2% or more about 99.5% or more or about 99.7% or more of the $C_3$ chlorinated alkene,
less than about 50000 ppm, less than about 25000 ppm, less than about 20000 ppm, less than about 10000 ppm, less than about 5000 ppm, less than about 2000 ppm, less than about 1000 ppm, less than about 500 ppm, less than about 200 ppm, or less than about 100 ppm of chlorinated alkane starting material,
less than about 50000 ppm, less than about 25000 ppm, less than about 20000 ppm, less than about 10000 ppm, less than about 5000 ppm, less than about 2000 ppm, less than about 1000 ppm, less than about 500 ppm, less than about 200 ppm, or less than about 100 ppm of chlorinated $C_4$ alkanes and $C_4$ alkenes less than about 1000 ppm, less than about 500 ppm, less than about 200 ppm, or less than about 100 ppm of chlorinated $C_{5-6}$ alkane impurities,
less than about 5000 ppm, 1000 ppm, less than about 500 ppm, less than about 200 ppm, or less than about 100 ppm of chlorinated alkene impurities (i.e. chlorinated alkenes other than the compound of interest),
less than about 1000 ppm, less than about 500 ppm, less than about 250 ppm, or less than about 100 ppm of oxygenated organic compounds,
less than about 500 ppm, less than about 200 ppm, less than about 100 ppm, less than about 50 ppm, less than about 20 ppm, less than about 10 ppm or less than about 5 ppm metal, and/or
less than about 100 ppm, less than about 50 ppm, less than about 20 ppm, less than about 10 ppm or less than about 5 ppm water.

According to a further aspect of the present invention, there is provided a process for preparing a hydrofluoroolefin or hydrochlorofluoroolefin comprising the step of providing a highly pure chlorinated alkene composition as discussed above, or as obtained from the dehydrochlorination process of the present invention, and converting the chlorinated alkene to a hydrofluoroolefin or hydrochlorofluoroolefin.

This conversion may be achieved through any process known to those skilled in the art. In embodiments of the invention, the conversion is carried out in a hydrofluorination plant.

In preferred embodiments, the chlorinated alkene present as the principal component of the composition has a dichlorinated terminal carbon atom, for example 1,1,3,3-tetrachloropropene and the hydrofluoroolefin or hydrochlorofluoroolefin preferably has a trifluorinated terminal carbon atom, for example 2,3,3,3-tetrafluoropropene, 1,3,3,3-tetrafluoropropene or 1-chloro-3,3,3-trifluoropropene.

The processes of the present invention also permit the preparation of highly pure combinations of $C_3$ chlorinated alkane isomers which find utility in downstream reactions.

Additionally, the processes of the present invention can employ such combinations as feedstocks in commercially viable processes.

Thus, according to a further aspect of the present invention, there is provided a composition (which may or may not be obtainable from the processes of the present invention) comprising a plurality of $C_3$ chlorinated alkane isomers, for example, 1,1,1,2,3-pentachloropropane and 1,1,1,3,3-pentachloropropane or 1,1,1,2,3-pentachloropropane and 1,1,2,2,3-pentachloropropane, at a purity (i.e. a content as percentage by weight) of about 95% or higher, about 97% or higher, about 99% or higher, about 99.5% or higher, about 99.7% or higher about 99.8% or higher, or about 99.9% or higher of the plurality of $C_3$ chlorinated alkane isomers and preferably further comprises:

less than about 10000 ppm, less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about 5 ppm of under chlorinated impurities, less than about 5000 ppm, less than about 2000 ppm, less than about 1000 ppm, less than about 500 ppm, less than about 200 ppm, less than about 100 ppm, less than about 50 ppm, less than about 20 ppm, less than about 100 ppm or less than about ppm of over chlorinated impurities, less than about 5000 ppm, less than about 2000 ppm, less than about 1000 ppm, less than about 500 ppm, less than about 200 ppm, less than about 100 ppm, less than about 50 ppm, less than about 20 ppm, less than about 100 ppm or less than about ppm of chlorinated alkene compounds, less than about 1000 ppm, less than about 500 ppm, less than about 200 ppm, less than about 100 ppm, less than about 50 ppm, less than about 20 ppm, less than about ppm or less than about 5 ppm of compounds having a different number of carbon atoms than the isomers, less than about 1000 ppm, less than about 500 ppm, less than about 200 ppm, less than about 100 ppm, less than about 50 ppm, less than about 20 ppm, less than about ppm less than about 5 ppm, or less than about 2 ppm of oxygenated organic impurities, less than about 500 ppm, less than about 200 ppm, less than about 100 ppm, less than about 50 ppm, less than about 20 ppm, less than about 10 ppm or less than about 5 ppm metal, and/or less than about 100 ppm, less than about 50 ppm, less than about 20 ppm, less than about 10 ppm or less than about 5 ppm water.

According to a further aspect of the present invention, there is provided a composition (which may or may not be obtained from the processes of the present invention) comprising a $C_3$ chlorinated alkane optionally selected from 1,1,1,2,3-pentachloropropane and 1,1,1,3,3-pentachloropropane and a $C_3$ chlorinated alkene optionally selected from 1,1,2,3-tetrachloro-1-propene, 1,1,3,3-tetrachloro-1-propene, and 1,3,3,3-tetrachloro-1-propene, the $C_3$ chlorinated alkane and the $C_3$ chlorinated alkene together having a purity of about 95% or higher, about 97% or higher, about 99% or higher, about 99.5% or higher, about 99.7% or higher, about 99.8% or higher or about 99.9%, the composition further comprising:

less than about 10000 ppm, less than about 5000 ppm, less than about 2000 ppm, less than about 1000 ppm, less than about 500 ppm, less than about 200 ppm, less than about 100 ppm, less than about 50 ppm, less than about 20 ppm, less than about ppm or less than about 5 ppm of $C_3$ chlorinated alkane compounds comprising less chlorine atoms than the first $C_3$ chlorinated alkane, less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about ppm of $C_3$ chlorinated alkane compounds comprising more chlorine atoms than the $C_3$ chlorinated alkane, less than about 5000 ppm, less than about 2000 ppm, less than about 1000 ppm, less than about 500 ppm, less than about 200 ppm, less than about 100 ppm, less than about 50 ppm, less than about 20 ppm, less than about 10 ppm or less than about ppm of chlorinated alkene compounds other than the $C_3$ chlorinated alkene compound, less than about 10000 ppm, less than about 5000 ppm, less than about 2000 ppm, less than about 1000 ppm, less than about 500 ppm, less than about 200 ppm, less than about 100 ppm, less than about 50 ppm, less than about 20 ppm, less than about ppm or less than about 5 ppm of compounds having a different number of carbon atoms than the $C_3$ chlorinated alkane compound, less than about 1000 ppm, less than about 500 ppm, less than about 200 ppm, less than about 100 ppm, less than about 50 ppm, less than about 20 ppm, less than about ppm less than about 5 ppm, or less than about 2 ppm of oxygenated organic impurities, less than about 500 ppm, less than about 200 ppm, less than about 100 ppm, less than about 50 ppm, less than about 20 ppm, less than about 10 ppm or less than about ppm metal, and/or less than about 100 ppm, less than about 50 ppm, less than about 20 ppm, less than about 10 ppm or less than about 5 ppm water.

As confirmed above, the compositions of the present invention, and the products obtained from the processes of the present invention, advantageously benefit from a combination of very high purity and acceptable impurities. This makes them well-suited for use in downstream reactions, particularly in the preparation of hydrofluorinated or hydrochlorofluorinated alkane or alkene compounds.

Thus, according to a further aspect of the present invention, there is provided the use of the compositions described herein, or the products of the processes described herein in the preparation of fluorinated alkane or alkene compounds. In embodiments of this aspect of the present invention, the fluorinated alkane or alkene compound may have a trifluorinated terminal carbon atom, for example 2,3,3,3-tetrafluoropropene (HFO-1234yf), 1,3,3,3-tetrafluoropropene (HFO-1234ze), 1-chloro-3,3,3-trifluoro-1-propene (HCFO-1233zd), 2-chloro-3,3,3-trifluoro-1-propene (HCFO- 1233xf), 1,2-dichloro-3,3,3-trifluoropropane (HCFC-243db), 2-chloro-2,3,3,3-tetrafluoropropane (HCFC-244bb), 1,1,1,2,2-pentafluoropropane (HFC-245cb), 1-chloro-1,3,3,3-tetrafluoropropane (HCFC-244fa) or 1,1,1,3,3-pentafluoropropane (HFC-245fa).

In a preferred aspect of this aspect of the invention, the dehydrochlorination step of the present invention results in the production of a high purity composition comprising 1,1,3,3,-tetrachloropropene, for example that disclosed above, which is used in the direct or indirect production of hydrofluoroolefins or hydrochlorofluoroolefins, preferably those including trifluorinated terminal carbon atoms such as 1-chloro-3,3,3-tetrafluoropropene, 2,3,3,3-tetrafluoropropene and/or 1,3,3,3-tetrafluoropropene.

The invention is further illustrated in the following Examples in which reference is made to the following figures.

EXAMPLES

Glossary: in following tables, the following nomenclature is used Short term Compound

| Short term | Compound |
|---|---|
| 1113-TeCPa | 1,1,1,3-tetrachloropropane |
| 1123-TeCPe | 1,1,2,3-tetrachloropropane |
| 1133-TeCPe | 1,1,3,3-tetrachloropropene |
| 1333-TeCPe | 1,3,3,3-tetrachloropropene |
| 11133-PCPa | 1,1,1,3,3-pentachloropropane |
| 11123-PCPa | 1,1,1,2,3-pentachloropropane |
| 111333-HCPa | 1,1,1,3,3,3-hexachloropropane |
| 111233-HCPa | 1,1,1,2,3,3-hexachloropropane |
| 111223-HCPa | 1,1,1,2,2,3-hexachloropropane |

Figure 1:
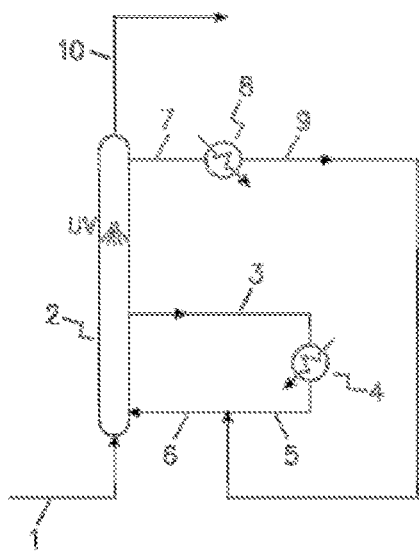
FIG. 1 is a schematic drawing of an arrangement that may be employed in the processes of the present invention to achieve chlorination of a $C_3$ chlorinated alkane starting material.

Example 1. Chlorination of 1,1,1,3-Tetrachloropropane to Produce a Mixture of Pentachloropropanes Chlorination was carried out as shown in FIG. 1 in a batch bubble column glass reactor (2) with external cooling circulations (3,7). The reactor was equipped with 250 W medium pressure mercury lamp immersed using quartz tube inside the column reactor. The cooling medium for coolers (4,8) was ethylene glycol solution. Gaseous chlorine (1) was introduced at the reactor bottom using a set of nozzles and liquid feedstock was initially filled using line (6). The temperature in the reactor was controlled to about 25° C.; the pressure in the reactor was atmospheric. The vent gas (10), hydrogen chloride with trace amounts of chlorine, was led to a caustic scrubber and the caustic was regularly analyzed for NaOCl and alkalinity in order to check HCl formation and chlorine loss via vent gas.

460.7 kg of 1,1,1,3-Tetrachloropropane with a purity of 98.4% was initially filled into the chlorination reactor. Chlorine gas (83.1 kg) was introduced into the chlorination zone at a feeding rate of 8 kg/h. The 1,1,1,3-tetrachloropropane starting material was produced using the process and purity profile as described in WO2016/058566.

The amount of hydrogen chloride produced was 39.8 kg and the loss of chlorine was almost zero. The molar ratio of chlorine:1,1,1,3-tetrachloropropane was 47%. After about 10 hours the reaction was stopped and 502.7 kg of produced reaction mixture was analyzed by GC to provide the following results:

| Compound | Amount (wt. %) |
|---|---|
| 1113-TeCPa | 53.98% |
| 11133-PCPa | 34.93% |
| 11123-PCPa | 9.31% |
| 111333-HCPa | 0.74% |
| 111233-HCPa | 0.58% |
| 111223-HCPa | 0.34% |

Calculated selectivity towards 11133PCPa was 79%.

As can be seen, control of the molar ratio of the starting material (1,1,1,3-tetrachloropropane):chlorinated alkane isomers (1,1,1,3,3-pentachloropropane and 1,1,1,2,3-pentachloropropane) was limited to 59:41 which advantageously prevented the formation of high amounts of over chlorinated impurities.

Example 2. Purification of the Reaction Mixture from Example 1

Figure 2:
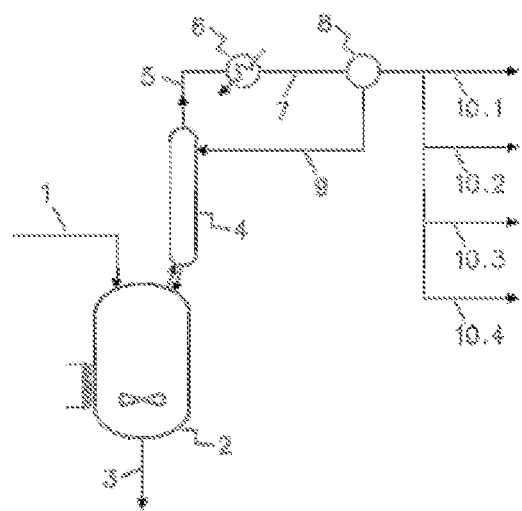
FIG. 2 is a schematic drawing of an arrangement that may be employed in the processes of the present invention to distill valuable product streams from a mixture comprising a plurality of $C_3$ chlorinated alkane isomers.

As shown in FIG. 2, a batch vacuum glass distillation column (4) with accessories (5, 6, 7, 8, 9) was filled with plastic rings equal to about 25 theoretical stages efficiency. The vacuum in the column was set on appropriate level to keep the bottom of the boiler (2) temperature below 110° C.

35.164 kg of reaction mixture was extracted from the reactor used in Example 1 and was initially filled to the column boiler (2) via line (1). Using reflux ratio of about 5 in sum, four fractions as distillates F1 (10.1), F2 (10.2), F3 (10.3), F4 (10.4.) and one fraction F5(DR) as distillation residue (3) were collected. The composition and mass of the fractions were following:

|  |  | Distillation Feed | F1 | F2 | F3 | F4 | F5(DR) |
|---|---|---|---|---|---|---|---|
| Mass | kg | 35.164 | 18.411 | 13.289 | 2.206 | 0.181 | 0.476 |
| 1113-TeCPa | % | 53.98 | 97.93 | 0.12 | 0.00 | 0.00 | 0.00 |
| 11133-PCPa | % | 34.93 | 1.80 | 92.95 | 0.02 | 0.01 | 0.00 |
| 11123-PCPa | % | 9.31 | 0.00 | 6.90 | 99.68 | 68.29 | 0.81 |

| | | Distillation Feed | F1 | F2 | F3 | F4 | F5(DR) |
|---|---|---|---|---|---|---|---|
| 111333-HCPa | % | 0.74 | | 0.00 | 0.22 | 28.76 | 26.05 |
| 111233-HCPa | % | 0.58 | | | | 0.15 | 45.72 |
| 111223-HCPa | % | 0.34 | | | | 0.05 | 26.02 | means concentration less than 0.005% wt., blank cell means not detectable=less than 1 ppm.

The following recycling scheme was then applied:
Fraction F1: unreacted starting material stream, to be recycled to the chlorination Example 1
Fraction F2: chlorinated alkane isomers product stream, to be used as feedstock for next process step (see Examples 3, 4, 5)
Fraction F3: single isomer product stream (second main product 11123-PCPa), to be used as feedstock for downstream processes e.g. as precursor of chlorinated or fluorinated alkenes.
Fraction F4: to be recycled to the next distillation trial according to this Example 2 in order to built up concentration of 111333-HCPa impurity and after that to be further treated using e.g. high temperature chlorinolysis process to recover chlorine value or to be incinerated
Fraction F5 distillation residue, to be further treated using e.g. high temperature chlorinolysis process to recover chlorine value or to be incinerated Considering the sum of 1,1,1,3,3- and 1,1,1,2,3-pentachloropropanes obtained, the calculated yield of distillation (without recycling scheme) is 99.45%

As can be seen, from the initial mixture which was subjected to distillation (comprising 1,1,1,3-tetrachloropropane starting material, 1,1,1,2,3-pentachloropropane, 1,1,1,3,3-pentachloropropane and over-chlorinated impurities specifically), the 1,1,1,3-tetrachloropropane feedstock is separated as a major fraction F1 and sent back to the chlorination reaction zone. Fraction F2 is a mixture of 1,1,1,2,3-pentachloropropane and 1,1,1,3,3-pentachloropropane, wherein the content of 1,1,1,2,3-pentachloropropane is reduced (owing to the extraction of high purity 1,1,1,2,3-pentachloropropane as fraction F3). Fraction F3 is high purity 1,1,1,2,3-pentachloropropane which is isolated as a useful product in downstream processes. Minor fractions F4 and F5 are retrieved, and are either recycled or sent for recovery of chlorine content for example in a high temperature chlorinolysis process.

The preparation of fraction F2 of 1,1,1,3,3-pentachloropropane and 1,1,1,2,3-pentachloropropane was configured to have greater selectivity towards the 1,1,1,3,3-pentachloropropane isomer as the end product of interest in this synthesis is its corresponding alkene, 1,1,3,3-tetrachloropropene (1230za) the production of which is discussed below. Importantly, fraction F2 is free of starting alkane material (1,1,1,3-tetrachloropropane, 250fb) as 250fb can form 1,1,3-trichloropropene in the downstream dehydrochlorination steps. Separation of 1,1,3-trichloropropene from the desired 1,1,3,3-tetrachloropropene is problematic as 1,1,3-trichloropropene is a more reactive chlorinated alkene and it can be a catalyst poison for downstream hydrofluorination processes, for example the conversion of 1,1,3,3-tetrachloropropene to e.g. 1,1,1-trifluoro-3-chloro-1-propene (HFCO-1233zd), 1,1,1,3-tetrafluoro-1-propene (HFO-1234ze), 1,1,1,3,3-pentafluoropropane (HFC-245fa) and mixtures thereof.

Figure 3:
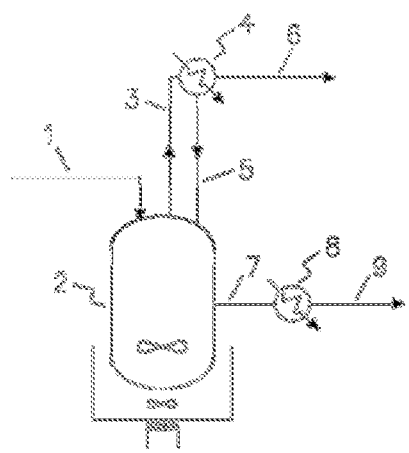
FIGS. 3 and 4 are schematic drawings of arrangements that may be employed in the processes of the present invention for selectively dehydrochlorinating one isomer present in a plurality of $C_3$ chlorinated alkane isomers.

Example 3. Highly Selective Dehydrochlorination of Mixture of 1,1,1,3,3- and 1,1,1,2,3-Pentachloropropanes Fraction F2 (10.2) from Example 2 was fed into a continuous stirred tank glass reactor (2) as shown in FIG. 3. The reactor (2) consisted of a four neck glass flask equipped with a magnetic stirrer, thermometer, back cooler (4), feed and discharge pipes and hot oil heating bath. The feedstock (1) consisted of fraction F2 and about 100 ppm (based on the feedstock) added catalyst (FeCl$_3$). Such a liquid feedstock was continuously fed by a dosing pump into the reactor. The formed HCl gas (3) was cooled down by means of a back cooler/condenser (4) and then (6) absorbed in an absorption column into the water to check the rate of HCl formation. The reaction mixture (7) was continuously automatically extracted from the reactor via a cooler (8) to the glass collection vessel (9) to keep the liquid level in the reactor on the constant value. Temperature of reaction was about 102° C., temperature of the subcooled reaction mixture was less than 20° C. and reaction pressure was atmospheric. The calculated mean residence time was 2:09 hour.

4230 g of fraction F2 from Example 2 with added catalyst was continuously fed into the reactor at a rate of 145 g/h. Then, in sum, 450 g HCl was produced and absorbed in the absorption column. 3724 g of product mixture was extracted and analyzed by GC to provide the following results:

| | Feed | Reaction mixture |
|---|---|---|
| 1333-TeCPe (%) | | 0.10 |
| 1133-TeCPe (%) | 0.02 | 69.58 |
| 1123-TeCPe (%) | | 0.20 |
| 11133-PCPa (%) | 92.95 | 22.96 |
| 11123-PCPa (%) | 6.90 | 7.00 |

Basic Parameters of Reaction Steps:

| | Reactor 1 |
|---|---|
| Mean residence time | 2:09 h |
| Temperature | 102° C. |
| Pressure | atm. |
| Calculated 11133-PCPa conversion | 75.3% |
| Calculated selectivity 1133- towards 1123-TeCPe | 99.7% |

As can be seen from this example, the selectivity of the dehydrochlorination step in favour of the production of 1,1,3,3-tetrachloropropene was very high, at 99.7%

Example 4. Highly Selective Catalytic Dehydrochloration of the Mixture of Pentachloropropanes from Example 2

Figure 4:
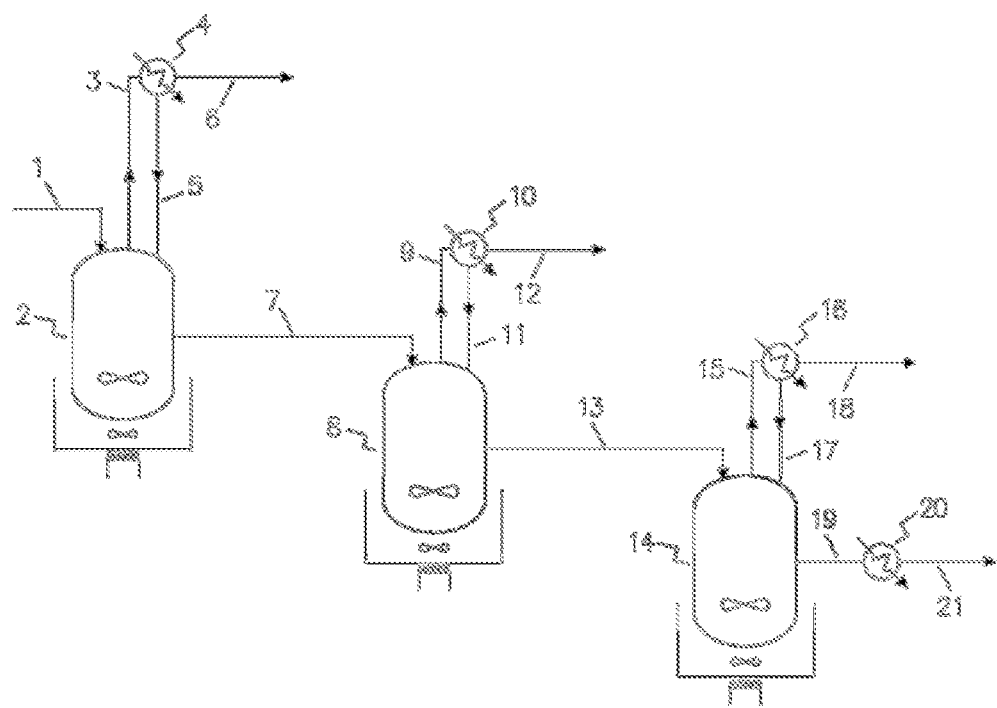

This dehydrochlorination step was carried out in a similar manner as described in Example 3 above, but in series or cascade of three continuously stirred tank glass reactors (2, 8, 14) as shown in FIG. 4. The liquid reaction mixture (7)

was continuously extracted via line (7) from first reactor (2) and then fed to the second reactor (8), and then from the second reactor to the third reactor (14) via line (13).

From the third reactor, the said liquid reaction mixture (19) was extracted via the cooler (20) and collected in a glass flask. Each reactor was equipped with the same accessories as in Example 3. Catalyst (FeCl$_3$) was added in the amount of 100 ppm only in the liquid feed (1) to the first reactor. Samples of reaction mixture were analyzed by GC upon extraction from each reactor. The formed hydrogen chloride gas (3, 9, 15) from each reactor was separately cooled down by means of a back cooler/condenser (4, 10, 16) and then (6, 12, 18) absorbed in separated absorption columns into the water to check the rate of HCl formation (and thus relate to the conversion) in each reactor. The operating temperature in the reactors was 101, 100 and 103° C., respectively. The temperature of the subcooled reaction mixture was less than 20° C. and the pressure was always atmospheric.

5301 g of mixture of fraction 2 (the chlorinated alkane isomers stream comprising pentachloropropanes) from Example 2 with added catalyst was continuously fed into the first reactor at a rate of 552 g/h. 679 g hydrogen chloride was produced and absorbed in three absorption columns and 4573 g of product mixture was extracted from the third reactor. This product mixture was analyzed by GC to provide the following results:

|  | Feed | Reactor 1 | Reactor 2 | Reactor 3 |
|---|---|---|---|---|
| 1333-TeCPe (%) |  | 0.11 | 0.13 | 0.06 |
| 1133-TeCPe (%) | 0.02 | 48.26 | 67.56 | 76.38 |
| 1123-TeCPe (%) |  | 0.07 | 0.12 | 0.15 |
| 11133-PCPa (%) | 92.95 | 44.27 | 24.89 | 16.12 |
| 11123-PCPa (%) | 6.90 | 7.14 | 7.16 | 7.12 |

Basic Parameters of Reaction Steps:

|  | Reactor 1 | Reactor 2 | Reactor 3 |
|---|---|---|---|
| Mean residence time | 0:29 h | 0:31 h | 0:35 h |
| Temperature | 101° C. | 100° C. | 103° C. |
| Pressure | atm. | atm. | atm. |
| Calculated 11133-PCPa cumulative conversions | 52.4% | 73.2% | 82.7% |
| Calculated cumulative selectivity 1133- towards 1123-TeCPe | 99.9% | 99.8% | 99.8% |

Examples 3 and 4 illustrate highly selective catalytic dehydrochlorination steps using a mixture of pentachloropropane isomers as a starting material. The isomeric ratio of 1,1,1,3,3-pentachloropropane to 1,1,1,2,3-pentachloropropane of 93:7 was achieved by the efficient distillation of the reaction mixture after chlorination which results in a single isomer stream being obtained which is rich in 1,1,1,2,3-pentachloropropane, as well as a plurality of C$_3$ chlorinated alkane isomer stream being obtained having the increased isomeric ratio of 1,1,1,3,3-pentachloropropane:1,1,1,2,3-pentachloropropane. As demonstrated, dehydrochlorination can be carried out either in one reactor as in Example 3 or in series of three reactors as shown in Example 4, where selectivity of 1,1,3,3-tetrachloropropene over 1,1,2,3-tetrachloropropene of 99.8% was achieved by higher feedstock conversion rate and lower residence time.

Example 5. Selective Dehydrochlorination of the Pentachloropropane Isomer Mixture Obtained in Example 1

Highly selective catalytic dehydrochlorination of mixture of pentachloropropanes was carried out in similar manner as in Example 4. However, a different feedstock was used, comprising a plurality of pentachloropropane isomers in the ratio in which they were produced in Example 1.

5879 g of the mixed pentachloropropane isomer feedstock (isomer ratio of 11133:11123-PCPa=78.95:20.97) with added catalyst was continuously fed into the first reactor at a rate of 920 g/h. 631 g of hydrogen chloride was produced and absorbed in three absorption columns. 5194 g of product mixture was obtained from the third reactor and analyzed by GC to provide the following results:

|  | Feed | Reactor 1 | Reactor 2 | Reactor 3 |
|---|---|---|---|---|
| 1333-TeCPe (%) |  | 0.11 | 0.07 | 0.08 |
| 1133-TeCPe (%) | 0.02 | 47.87 | 61.43 | 66.55 |
| 1123-TeCPe (%) |  | 0.29 | 0.43 | 0.51 |
| 11133-PCPa (%) | 78.95 | 30.26 | 16.58 | 11.26 |
| 11123-PCPa (%) | 20.97 | 21.24 | 21.20 | 21.25 |

Basic Parameters of Reaction Steps:

|  | Reactor 1 | Reactor 2 | Reactor 3 |
|---|---|---|---|
| Mean residence time | 0:17 h | 0:18 h | 0:20 h |
| Temperature | 100° C. | 101° C. | 101° C. |
| Pressure | atm. | atm. | atm. |
| Calculated 11133-PCPa cumulative conversions | 61.7% | 79.0% | 85.7% |
| Calculated cumulative selectivity 1133- towards 1123-TeCPe | 99.4% | 99.3% | 99.2% |

Example 5 illustrates a further highly selective dehydrochlorination step.

Selectivity of the desired C$_3$ chlorinated alkene of 99.2% was achieved.

Isomer Selectivity Comparison Table:

|  | Example 3 | Example 4 | Example 5 |
|---|---|---|---|
| TeCPe isomer selectivity | 99.7% | 99.8% | 99.2% |
| 11123-PCPa conversion (loss) | 3.32% | 2.58% | 2.95% |

Example 6. Aqueous Treatment of C$_3$ Chlorinated Alkene-Containing Mixtures

Figure 5:
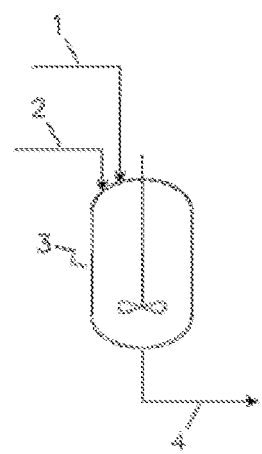
FIG. 5 is a schematic drawing of an arrangement that may be employed in the processes of the present invention in which a mixture comprising a $C_3$ chlorinated alkene may be subjected to aqueous treatment.

The reaction mixtures obtained from the dehydrochlorination steps performed in Examples 3, 4 and 5 were purified using a water treatment step carried out in a batch stirred glass reactor equipped with a high rotation-speed stirrer and temperature control system as shown on FIG. 5. 2% hydrogen chloride solution was mixed with distilled water (2). Cold mixture obtained from the dehydrochlorination steps (1) was mixed with the acidic solution in a 1:1 ratio and the resulting mixture stirred for about 5 hours. This aqueous treatment results in deactivation of catalytic system and hydrolysis and removal of medium-polar or polar compounds, particularly oxygenated, chlorinated byproducts. This treatment is conducted at a temperature of about 20-25° C. and preferably not more than about 50° C. After stirring, the stirrer was stopped and mixture was separated into two layers—an upper aqueous layer and a lower organic layer. The lower layer was then extracted from the reactor (4) and dried using calcium chloride. The dried organic layer was then subjected to the distillation step in Example 7.

Figure 6:
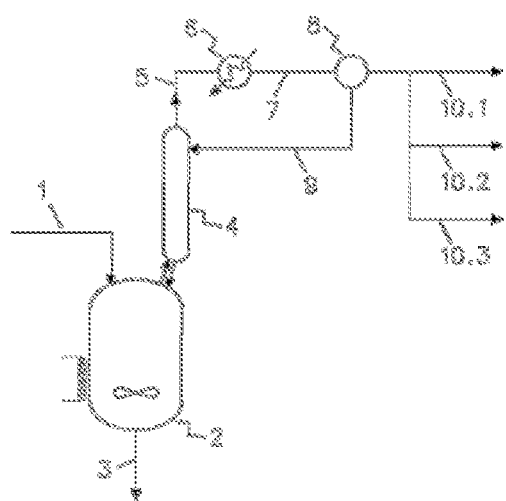
FIG. 6 is a schematic drawing of an arrangement that may be employed in the processes of the present invention to distill valuable product streams from a mixture comprising a $C_3$ chlorinated alkene.

Example 7. Distillation of Aqueous Treated C$_3$ Chlorinated Alkene Containing Mixture Following the aqueous treatment step of Example 6, purification of the mixture obtained in Example 4 was efficiently carried out in a batch vacuum glass distillation column (4) with accessories as shown in FIG. 6.

The column was filled with ceramic Berl saddles equal to about 30 theoretical stages efficiency. The vacuum was set on appropriate level to keep the bottom of the boiler at a temperature below 110° C. 6430 g of the chlorinated alkene-containing mixture (1) was fed to the column boiler (2). Three fractions as distillates F1(10.1), F2(10.2), F3(10.3) and one fraction F4(DR) as distillation residue were collected (3) using a reflux ratio of about 5. The composition and mass of the fractions were as follows:

|  | feed | F 1 | F 2 | F 3 | F 4(DR) |
|---|---|---|---|---|---|
| mass (g) | 6430 | 326 | 3905 | 435 | 1461 |
| lights (%) | 0.12 | 1.53 | 0.05 | 0.26 | 0.01 |
| 1333-TeCPe (%) | 0.05 | 0.74 | 0.56 | 0.05 | ND |
| 1133-TeCPe (%) | 75.22 | 97.66 | 99.36 | 66.90 | 0.14 |
| 1123-TeCPe (%) | 0.14 | 0.01 | 0.01 | 2.23 | 0.04 |
| 11133-PCPa (%) | 17.26 | ND | <0.005 | 30.08 | 67.38 |
| 11123-PCPa (%) | 7.15 | ND | ND | 0.00 | 32.08 |

The fractions were then processed as follows:

Fraction F1: was recycled for use in subsequent distillation steps corresponding to those carried out in this Example 7 in order to build up the concentration of light ends which can subsequently be purged and further treated using e.g. high temperature chlorinolysis process or incineration Fraction F2 is the main product stream comprising the target chlorinated alkene (1,1,3,3-tetrachloropropene at high purity) with acceptably low levels of 1,1,2,3-tetrachloropropene. This product stream can be used as a feedstock in downstream processes e.g. as precursor of hydrofluorinated alkenes.

Fraction F3: was recycled for use in subsequent distillation steps corresponding to those carried out in this example in order to build up the concentration of 1,1,2,3-tetrachloropropene and other impurities which can subsequently be treated using e.g. high temperature chlorinolysis process or incineration, or which can be fed back for use in a chlorination step of the present invention, e.g. that described in Example 1.

Fraction F4(DR) was recycled to the distillation step of Example 2.

Calculated yield of distillation (without recycling scheme): 80.2%

Example 8. Influence of Molar Ratio of C$_3$ Chlorinated Alkane Starting Material:C$_3$ Chlorinated Alkane Isomer in Reaction Mixture During Chlorination Step Chlorination of 1,1,1,3-tetrachloropropane to produce a mixture comprising 1,1,1,3,3-pentachloropropane and 1,1,1,2,3-pentachloropropane was carried out in a glass batch stirred reactor.

The reactor was equipped with a 125 W medium pressure mercury lamp. Temperature in the reactor was maintained at about 12° C. and the pressure in the reactor was atmospheric. The vent gas was bubbled into a caustic scrubber and this caustic was regularly analysed with respect to alkalinity in order to check the amount of hydrogen chloride formation. Chlorine gas was introduced into the reactor via a glass dip pipe with nozzle and was totally consumed in the reactor.

504.4 g of 1,1,1,3-tetrachloropropane starting material with a purity of 99.9% was initially filled to the reactor. 198 g of chlorine was likewise fed at a rate of 33 g per hour. Samples from the reactor were taken regularly and were analyzed by GC to provide the following results:

|  | Amount of chlorine based on stoichiometry ratio | | | | |
|---|---|---|---|---|---|
|  | 20% | 40% | 60% | 80% | 100% |
| Ratio of 1113-TeCPa starting material towards all PCPa isomers | 82:18 | 64:36 | 45:55 | 28:72 | 12:88 |
| Ratio of 11123-PCPa towards all PCPa isomers (%) | 19.2 | 19.3 | 19.3 | 18.7 | 17.7 |
| Ratio of HCPa towards all PCPa isomers (%) | 1.0 | 2.3 | 4.4 | 7.7 | 15.0 |
| Ratio of 111333-HCPa towards 11123-PCPa (%) | 2.1 | 5.1 | 10.2 | 18.9 | 39.9 |

From the above results, it is observed that molar ratio between feedstock 1,1,1,3-tetrachloropropane and the isomeric product mixture significantly influences the formation of unwanted hexachloropropane compounds and thus yield. The undesired 1,1,1,3,3,3-hexachloropropane, which has boiling point close to 1,1,1,2,3-pentachloropropane, is difficult to remove and is also extremely reactive in the presence of trace of metals. As is apparent from the data shown here, control of the conversion of the starting material prevents formation of these problematic impurities.

Thus to minimise production of problematic over chlorinated impurities, the conversion of the feedstock chloroalkane to the product chloropropanes, represented by the molar ratio between the feedstock chloroalkane and product chloropropanes, should be kept such that it does not exceed about 40:60, and more advantageously does not exceed about 60:40.

Example 9. Influence of Reaction Temperature During Chlorination

A series of chlorinations of 1,1,1,3-tetrachloropropane at a range of temperatures to produce a mixture of 1,1,1,3,3-pentachloropropane and 1,1,1,2,3-pentachloropropane were carried out in a glass batch stirred reactor. The reactor was equipped with a 125 W medium pressure mercury lamp. The operating temperature in the reactor was maintained at 10° C., 25° C., 50° C., 60° C., 95° C. and 115° C. Pressure in the reactor was atmospheric. The vent gas was bubbled into a caustic scrubber and the caustic was regularly analysed for the alkalinity in order to check hydrogen chloride formation. Chlorine was introduced into the reactor via glass dip pipe with nozzle and was totally consumed in the reactor.

600 g of 1,1,1,3-tetrachloropropane with a purity of 99.9% was initially filled into the reactor. Chlorine was fed in to the reaction in a quantity equal to 60% by stoichiometry at a feeding rate of 100 grams per hour. The reaction mixture after completion was sampled from the reactor and was analysed by GC. The GC analytical results and kinetic study results are shown in the following tables:

|                                                    | Example No. |        |        |        |        |         |
| -------------------------------------------------- | ----------- | ------ | ------ | ------ | ------ | ------- |
|                                                    | 9.1         | 9.2    | 9.3    | 9.4    | 9.5    | 9.6     |
| Reaction temperature                               | 10° C.      | 25° C. | 50° C. | 60° C. | 95° C. | 115° C. |
| 1113-TeCPa (%)                                     | 44.13       | 42.61  | 43.69  | 43.56  | 47.18  | 44.11   |
| 11133-PCPa (%)                                     | 42.15       | 43.20  | 41.77  | 41.31  | 37.93  | 39.63   |
| 11123-PCPa (%)                                     | 10.19       | 10.98  | 10.98  | 11.42  | 10.26  | 10.99   |
| 111333-HCPa (%)                                    | 0.97        | 1.11   | 1.17   | 1.16   | 1.38   | 1.41    |
| 111233-HCPa (%)                                    | 0.76        | 0.88   | 0.99   | 1.03   | 1.51   | 1.66    |
| 111223-HCPa (%)                                    | 0.45        | 0.49   | 0.51   | 0.51   | 0.39   | 0.26    |
| Other (%)                                          | 1.36        | 0.74   | 0.89   | 1.00   | 1.35   | 1.94    |
| Reaction temperature                               | 10° C.      | 25° C. | 50° C. | 60° C. | 95° C. | 115     |
| Ratio of 11123-PCPa towards all PCPa isomers (%)   | 19.47       | 20.27  | 20.82  | 21.66  | 21.29  | 21.71   |
| Ratio of HCPa isomers towards PCPa isomers (%)     | 4.15        | 4.56   | 5.05   | 5.12   | 6.81   | 6.58    |
| Ratio of all heavies incl. HCPa isomers towards PCPa isomers (%) | 4.24 | 4.57 | 5.10 | 5.14 | 7.52 | 8.07 |

The above results demonstrate that reaction temperature in the chlorination zone influences the rate of formation of the hexachloropropanes and thus yield. The pentachloropropane isomeric selectivity remains relatively stable across the range of temperatures (i.e. surprisingly, selectivity cannot be controlled by the temperature in this particular). Accordingly, for the efficient synthesis of 1,1,1,3,3-pentachloropropane modest operating temperatures are preferred, e.g. below 60° C. or more preferably below 40° C.

Example 10. Continuous Chlorination of 1,1,1,3-Tetrachloropropane to Produce Isomer Mix The chlorination of 1,1,1,3-tetrachloropropane to produce a mixture comprising 1,1,1,3,3-pentachloropropane and 1,1,1,2,3-pentachloropropane was carried out continuously in a glass CSTR stirred reactor.

The reactor consisted of a six-neck glass flask, equipped with a mechanical stirrer, a back-cooler, sets of inlets and outlet pipe connections, a thermos-probe and a 125 W high pressure mercury lamp housed in a quartz glass pipe and immersed into the reactor. The temperature in the reactor was maintained using a thermostat. The pressure in the reactor was atmospheric. The vent gas was linked through the back cooler into a HCl scrubber and then into a caustic scrubber. Both scrubbers were regularly analysed with respect to HCl and the chlorine content to monitor the amount of HCl formed as well as any unreacted chlorine. Chlorine gas was introduced into the reactor via a glass dip pipe with a nozzle outlet and the chlorine was almost totally consumed in the reactor.

The liquid feed was introduced in the reactor using a metering pump. The liquid reaction mixture left the reactor via an overflow pipe and passed into a collecting tank. Both the liquid feed mixture and chlorine were monitored by weight. The reaction mixture was analysed by GC.

The temperature in the reactor was about 34° C. There was no metal based catalyst employed in the liquid feed. Mean residence time in reactor was about 63 minutes. The molar amount of chlorine dosed based on the moles of liquid 1,1,1,3-tetrachloropropane introduced was about 22%. The results (in molar percentages) after reaching steady state are shown the following table:

| Example No. FeCl$_3$ = 0   | Example 10 |
| -------------------------- | ---------- |
| Reactor temperature (° C.) | 34.1       |
| Mean residence time (h)    | 1:03       |

-continued

| Example No. FeCl$_3$ = 0                            | Example 10 |
| --------------------------------------------------- | ---------- |
| Chlorine feed rate (mol % towards 1,1,1,3-TCPa)     | 22.0       |
| 1,1,1,3-TCPa conversion (mol %)                     | 19.2       |
| Ratio 11133-PCPa:11123 PCPa                         | 79.1:20.9  |
| Mol % byproducts:all isomers PCPa                   | 2.41       |

As shown in this table, the control of conversion of the starting material to the pentachloropropane isomers by limiting the feed of chlorine resulted in the formation of low levels of impurities, and a high selectivity for 1,1,1,3,3-pentachloropropane.

Full details of the composition obtained in this example are provided below. As can be seen, the reaction was highly selective towards the two pentachloropropane isomers of interest, 1,1,1,2,3-pentachloropropane and 1,1,1,3,3-pentachloropropane. In other words, very low levels of hexachlorinated propane impurities were produced and no detectable levels of pentachloropropane isomers other than the isomers of interest were obtained.

|            | Example No. 10   |
| ---------- | ---------------- |
| Compound   | Amount (wt. %)   |
| 113-TCPe   | 0.004            |
| 1333-TeCPe | na               |
| 1133-TeCPe | 0.000            |
| 1113-TeCPa | 77.857           |
| 1123-TeCPe | na               |
| 11133-PCPa | 17.018           |
| 11123-PCPa | 4.490            |
| 111333-HCPa| 0.280            |
| 111233-HCPa| 0.194            |
| 111223-HCPa| 0.124            |

Example 11. Influence of Catalyst and Temperature

The chlorination of 1,1,1,3-tetrachloropropane to produce a mixture comprising 1,1,1,3,3-pentachloropropane and 1,1,1,2,3-pentachloropropane was carried out continuously in a glass CSTR stirred reactor.

The reactor consisted of a six-neck glass flask, equipped with a mechanical stirrer, a back-cooler, sets of inlets and outlet pipe connections, a thermos-probe and 125 W high pressure mercury lamp housed in a quartz glass pipe and immersed into the reactor. The temperature in the reactor was maintained using a thermostat. The pressure in the reactor was atmospheric. The vent gas was linked through the back cooler into a HCl scrubber and then into a caustic scrubber. Both scrubbers were regularly analysed with respect to HCl and the chlorine content to monitor the amount of HCl formed as well as any unreacted chlorine. Chlorine gas was introduced into the reactor via a glass dip pipe with a nozzle outlet and the chlorine was almost totally consumed in the reactor.

The liquid feed was introduced in the reactor using a metering pump. The liquid reaction mixture left the reactor via an overflow pipe and passed into a collecting tank. Both the liquid feed mixture and chlorine were monitored by weight. A defined amount of hydrochloric acid was added into the reaction mixture collecting tank in order to de-activate the metal-based catalyst. Both the liquid feed mixture and chlorine were monitored by weight. The reaction mixture was analysed by GC.

The liquid feed was initially dried by $CaCl_2$ and, after filtration, doped by a defined amount of the metallic catalyst (anhydrous $FeCl_3$). This liquid feed was then held under a dry nitrogen atmosphere in order to prevent contamination by atmospheric moisture. The content of moisture in the liquid feed was about 12-46 ppmw (trial to trial). The content of 1,1,1,3-tetrachloropropane in the feed was more than 99.9%.

For the first trial, a range of temperatures were employed, namely about 40° C., 55° C., 90° C., 105° C. respectively. The amount of anhydrous $FeCl_3$ in the liquid feed was 12.5 ppmw. Mean residence time in reactor was about 30 minutes. The molar amount of chlorine dosed based on the moles of liquid 1,1,1,3-tetrachloropropane introduced was about 20%. The results after reaching steady state are shown the following table (all ratios in molar percent).

| Example No. | 11.1 | 11.2 | 11.2 | 11.4 |
|---|---|---|---|---|
| Reactor temperature (° C.) | 41.2 | 84.7 | 90.1 | 105.1 |
| Mean residence time (h) | 0:32 | 0:32 | 0:31 | 0:31 |
| Chlorine feed rate (mol % towards 1,1,1,3-TCPa) | 19.7 | 19.7 | 19.4 | 19.8 |
| 1,1,1,3-TCPa conversion (mol %) | 17.2 | 17.5 | 17.3 | 20.7 |
| Ratio 11133-PCPa:11123 PCPa | 78.9:21.1 | 70.8:29.2 | 64.1:35.9 | 17.8:82.2 |
| % byproducts:all isomers PCPa | 2.28 | 2.97 | 3.25 | 3.61 |

As can be seen, isomeric selectivity can be influenced by temperature control. Again, by minimising the conversion of the starting material to the isomers of interest (through control of the amount of chlorine provided), this provides control over the levels of impurities that are formed.

The following table illustrates the full compositions obtained from the runs in this example. As can be seen, advantageously, very low levels of hexachlorinated propanes were obtained. Further, no pentachloropropane isomers other than the isomers of interest (1,1,1,3,3-pentachloropropane and 1,1,1,2,3-pentachloropropane) were obtained. Thus, a very high selectivity towards those isomers was advantageously achieved.

| | Example No. | | | |
|---|---|---|---|---|
| | 11.1 | 11.2 | 11.3 | 11.4 |
| Compound | Amount (wt. %) | | | |
| 113-TCPe | 0.000 | 0.055 | 0.125 | 2.502 |
| 1333-TeCPe | 0.002 | 0.002 | 0.002 | 0.008 |
| 1133-TeCPe | 0.000 | 0.006 | 0.016 | 0.138 |
| 1113-TeCPa | 80.078 | 79.796 | 79.981 | 77.118 |
| 1123-TeCPe | na | 0.017 | 0.024 | 0.051 |
| 11133-PCPa | 15.282 | 13.764 | 12.281 | 3.466 |
| 11123-PCPa | 4.088 | 5.690 | 6.871 | 15.985 |
| 111333-HCPa | 0.214 | 0.210 | 0.170 | 0.021 |
| 111233-HCPa | 0.163 | 0.300 | 0.376 | 0.568 |
| 111223-HCPa | 0.108 | 0.106 | 0.112 | 0.054 |

Example 12. Influence of Conversion of Starting Material and Chlorine Feed on Byproduct Formation Chlorination of 1,1,1,3-tetrachloropropane to produce a mixture comprising 1,1,1,3,3-pentachloropropane and 1,1,1,2,3-pentachloropropane was carried out according to Example 10, but with an increased amount of chlorine, to increase the conversion of 1,1,1,3-tetrachloropropane. The molar amount of chlorine dosed based on the moles of 1,1,1,3-tetrachloropropane was about 40%. The results after reaching steady state are shown in the following table (all ratios in molar percent).

| Example No. | 12.1 | 12.2 | 12.3 | 12.4 |
|---|---|---|---|---|
| Reactor temperature (° C.) | 80.5 | 84.9 | 89.8 | 94.9 |
| Mean residence time (h) | 0:30 | 0:30 | 0:30 | 0:31 |
| Chlorine feed rate (mol % towards 1,1,1,3-TCPa) | 38.8 | 38.8 | 39.4 | 39.4 |
| 1,1,1,3-TCPa conversion (mol %) | 33.5 | 33.9 | 34.9 | 33.3 |
| Ratio 11133-PCPa:11123 PCPa | 78.1:21.9 | 75.1:24.9 | 70.6:29.4 | 64.7:35.3 |
| % byproducts:all isomers PCPa | 6.23 | 6.69 | 7.19 | 7.60 |

It can be seen that, in comparison to Example 10, the amount of formed byproducts, e.g. 111333-HCPa, is higher when using a greater molar ratio of chlorine 1,1,1,3-TCPa in the feed to the reactor.

The following table illustrates the full compositions obtained from the runs in this example. As can be seen, advantageously, very low levels of hexachlorinated propanes were obtained. Further, no pentachloropropane isomers other than the isomers of interest (1,1,1,3,3-pentachloropropane and 1,1,1,2,3-pentachloropropane) were obtained. Thus, a very high selectivity towards those isomers was advantageously achieved.

| | Example No. | | | |
|---|---|---|---|---|
| | 12.1 | 12.2 | 12.3 | 12.4 |
| Compound | Amount (wt. %) | | | |
| 113-TCPe | 0.012 | 0.021 | 0.046 | 0.020 |
| 1333-TeCPe | na | na | na | na |
| 1133-TeCPe | 0.005 | 0.006 | 0.010 | 0.012 |
| 1113-TeCPa | 62.312 | 61.896 | 60.826 | 62.476 |
| 1123-TeCPe | na | na | na | 0.035 |
| 11133-PCPa | 27.418 | 26.510 | 25.484 | 22.307 |
| 11123-PCPa | 7.685 | 8.795 | 10.587 | 12.147 |

|          | Example No. |       |       |       |
|----------|-------|-------|-------|-------|
|          | 12.1  | 12.2  | 12.3  | 12.4  |
| Compound | Amount (wt. %) | | | |
| 111333-HCPa | 1.055 | 1.042 | 0.953 | 0.754 |
| 111233-HCPa | 0.949 | 1.112 | 1.384 | 1.551 |
| 111223-HCPa | 0.471 | 0.495 | 0.557 | 0.551 |

Example 13. Influence of Conversion of 1,1,1,3-Tetrachloropropane and Residence Time Chlorination of 1,1,1,3-tetrachloropropane to produce a mixture comprising 1,1,1,3,3-pentachloropropane and 1,1,1,2,3-pentachloropropane was carried out according to Example 10. However, an increased amount of chlorine was introduced in order to increase the conversion of feedstock 1,1,1,3-tetrachloropropane. The molar amount of chlorine dosed based on the moles of 1,1,1,3-tetrachloropropane was about 40%. The mean residence time was about 54 minutes. The results after reaching steady state are shown the following table (all ratios in molar percent).

| Example No. | 13.1 | 13.2 | 13.3 | 13.4 |
|---|---|---|---|---|
| Reactor temperature (° C.) | 80.2 | 85.0 | 90.1 | 94.8 |
| Mean residence time (h) | 0:54 | 0:54 | 0:54 | 0:55 |
| Chlorine feed rate (mol % towards 1,1,1,3-TCPa) | 39.4 | 39.3 | 39.1 | 40.6 |
| 1,1,1,3-TCPa conversion (mol %) | 34.5 | 34.8 | 34.9 | 36.3 |
| Ratio 11133-PCPa:11123 PCPa | 73.6:26.4 | 67.6:32.4 | 54.3:45.7 | 34.4:65.6 |
| % byproducts:all isomers PCPa | 6.87 | 7.35 | 7.88 | 7.39 |

In comparison to the results obtained in Examples 10 and 11, the amount of byproducts formed is greater when conversion of the 1,1,1,3-tetrachloropropane starting material to the isomers of interest is increased and when a higher amount of chlorine is fed into the system. As can also be seen, the selectivity towards 1,1,1,2,3-pentachloropropane is influenced by residence time.

The following table illustrates the full compositions obtained from the runs in this example. As can be seen, advantageously, low levels of hexachlorinated propanes were obtained. Further, no pentachloropropane isomers other than the isomers of interest (1,1,1,3,3-pentachloropropane and 1,1,1,2,3-pentachloropropane) were obtained. Thus, a very high selectivity towards those isomers was advantageously achieved.

|          | Example No. |       |       |       |
|----------|-------|-------|-------|-------|
|          | 13.1  | 13.2  | 13.3  | 13.4  |
| Compound | Amount (wt. %) | | | |
| 113-TCPe | 0.029 | 0.061 | 0.230 | 1.313 |
| 1333-TeCPe | na | 0.000 | 0.001 | 0.004 |
| 1133-TeCPe | 0.006 | 0.012 | 0.029 | 0.124 |
| 1113-TeCPa | 61.243 | 60.912 | 60.859 | 59.646 |
| 1123-TeCPe | 0.017 | 0.023 | 0.036 | 0.053 |
| 11133-PCPa | 26.372 | 24.297 | 19.348 | 12.302 |
| 11123-PCPa | 9.473 | 11.655 | 16.270 | 23.473 |
| 111333-HCPa | 1.007 | 0.882 | 0.570 | 0.301 |
| 111233-HCPa | 1.208 | 1.470 | 1.901 | 2.079 |
| 111223-HCPa | 0.534 | 0.551 | 0.610 | 0.490 |

Example 14. Influence of Increased Amount of Catalyst

Chlorination of 1,1,1,3-tetrachloropropane to produce a mixture comprising 1,1,1,3,3-pentachloropropane and 1,1,1,2,3-pentachloropropane was carried out according to Example 10, but with increased amount of the catalyst FeCl$_3$ in the amount of 50 ppmw into the liquid feedstock. The results after reaching steady state are shown the following table (all ratios in molar percent).

| Example No. | 14.1 | 14.2 | 14.3 | 14.4 |
|---|---|---|---|---|
| Reactor temperature (° C.) | 60.2 | 70.0 | 80.0 | 84.8 |
| Mean residence time (h) | 0:32 | 0:32 | 0:32 | 0:33 |
| Chlorine feed rate (mol % towards 1,1,1,3-TCPa) | 19.3 | 19.2 | 19.3 | 19.8 |
| 1,1,1,3-TCPa conversion (mol %) | 17.2 | 17.2 | 17.3 | 19.2 |
| Ratio 11133-PCPa:11123 PCPa | 75.5:24.5 | 69.6:30.4 | 47.9:52.1 | 33.2:66.8 |
| % byproducts:all isomers PCPa | 2.46 | 2.83 | 3.28 | 3.46 |

In comparison to Example 10, it can be seen that the increased amount of catalyst used permits chlorination to proceed at lower reaction temperature, without any significant change in isomeric selectivity.

The following table illustrates the full compositions obtained from the runs in this example. As can be seen, advantageously, very low levels of hexachlorinated propanes were obtained. Further, no pentachloropropane isomers other than the isomers of interest (1,1,1,3,3-pentachloropropane and 1,1,1,2,3-pentachloropropane) were obtained. Thus, a very high selectivity towards those isomers was advantageously achieved.

|          | Example No. |       |       |       |
|----------|-------|-------|-------|-------|
|          | 14.1  | 14.2  | 14.3  | 14.4  |
| Compound | Amount (wt. %) | | | |
| 113-TCPe | 0.000 | 0.042 | 0.332 | 1.955 |
| 1333-TeCPe | na | na | 0.002 | 0.008 |
| 1133-TeCPe | 0.002 | 0.005 | 0.021 | 0.094 |
| 1113-TeCPa | 80.118 | 80.097 | 80.068 | 78.615 |
| 1123-TeCPe | na | na | 0.008 | 0.023 |
| 11133-PCPa | 14.568 | 13.349 | 9.020 | 6.143 |
| 11123-PCPa | 4.718 | 5.837 | 9.822 | 12.380 |
| 111333-HCPa | 0.210 | 0.189 | 0.095 | 0.059 |
| 111233-HCPa | 0.206 | 0.287 | 0.455 | 0.479 |
| 111223-HCPa | 0.117 | 0.136 | 0.127 | 0.092 |

Example 15. Continuous Chlorination Zones Operated in Sequence

Chlorination of 1,1,1,3-tetrachloropropane to produce a mixture comprising 1,1,1,3,3-pentachloropropane and 1,1, 1,2,3-pentachloropropane was carried out continuously in a reactor according to the procedure set out above in Example 10. Chlorination of the 1,1,1,3-tetrachloropropane was carried out in two CSTR reactors operated in sequence. The reaction mixture from the first CSTR was collected and then used as a liquid feedstock for the second CSTR. The total amount of 20 mol % of chlorine was added together in two steps. The results after reaching steady state are shown the following table (all ratios in molar percent).

| Example No. | 15.1 | 15.2 |
|---|---|---|
| Cascade step | 1 | 2 |
| Reactor temperature (° C.) | 35 | 34 |
| Mean residence time (h) | 1:01 | 1:00 |
| Chlorine feed rate (mol % towards 1,1,1,3-TCPa) | 10.3 | 11.1 |
| 1,1,1,3-TCPa conversion (mol %) | 9.4 | 19.5 |
| Ratio 11133-PCPa:11123 PCPa | 79.2:20.8 | 79.1:20.9 |
| % byproducts:all isomers PCPa | 0.90 | 1.75 |

As can be seen by comparing these results from those obtained in Example 10, conducting the chlorination reaction in two chlorination zones operated in sequence produces less by-products while achieving the same degree of conversion.

| | Example No. | |
|---|---|---|
| | 15.1 | 15.2 |
| Compound | Amount (wt. %) | |
| 113-TCPe | 0.004 | 0.009 |
| 1333-TeCPe | na | na |
| 1133-TeCPe | 0.001 | 0.001 |
| 1113-TeCPa | 89.054 | 77.588 |
| 1123-TeCPe | na | na |
| 11133-PCPa | 8.596 | 17.357 |
| 11123-PCPa | 2.258 | 4.581 |
| 111333-HCPa | 0.057 | 0.204 |
| 111233-HCPa | 0.032 | 0.141 |
| 111223-HCPa | 0.024 | 0.085 |

The invention claimed is:

1. A process for producing a reaction mixture comprising a plurality of $C_3$ chlorinated alkane isomers comprising chlorinating a $C_3$ chlorinated alkane starting material in a chlorination zone to produce the plurality of $C_3$ chlorinated alkane isomers, the plurality of $C_3$ chlorinated alkane isomers each having at least one more chlorine atom than the $C_3$ chlorinated alkane starting material, wherein the concentration of the $C_3$ chlorinated alkane starting material is controlled such that conversion of the $C_3$ chlorinated alkane starting material to the plurality of $C_3$ chlorinated alkane isomers, represented by the molar ratio of the $C_3$ chlorinated alkane starting material:$C_3$ chlorinated alkane isomers in the reaction mixture present in the chlorination zone, does not exceed about 40:60, wherein said plurality of $C_3$ chlorinated alkane isomers comprises a first isomer and a second isomer, and wherein the molar ratio of the first isomer:second isomer in the plurality of isomers produced in the chlorination zone is 40:60 to about 60:40.

2. A process for producing a reaction mixture comprising a plurality of $C_3$ chlorinated alkane isomers comprising chlorinating a $C_3$ chlorinated alkane starting material in a chlorination zone to produce the plurality of $C_3$ chlorinated alkane isomers, the plurality of $C_3$ chlorinated alkane isomers each having at least one more chlorine atom than the $C_3$ chlorinated alkane starting material, wherein the concentration of the $C_3$ chlorinated alkane starting material is controlled such that conversion of the $C_3$ chlorinated alkane starting material to the plurality of $C_3$ chlorinated alkane isomers, represented by the molar ratio of the $C_3$ chlorinated alkane starting material:$C_3$ chlorinated alkane isomers in the reaction mixture present in the chlorination zone, does not exceed about 40:60, wherein the reaction mixture is extracted from the chlorination zone and subjected to subsequent chlorination steps in 1, 2, 3, or 4 sequentially arranged downstream chlorination zones, wherein the molar ratio of the $C_3$ chlorinated alkane starting material:$C_3$ chlorinated alkane isomers in the reaction mixture present in any of the downstream chlorination zones does not exceed about 40:60.

3. A process for producing a reaction mixture comprising a plurality of $C_3$ chlorinated alkane isomers comprising chlorinating a $C_3$ chlorinated alkane starting material in a chlorination zone to produce the plurality of $C_3$ chlorinated alkane isomers, the plurality of $C_3$ chlorinated alkane isomers each having at least one more chlorine atom than the $C_3$ chlorinated alkane starting material, wherein the concentration of the $C_3$ chlorinated alkane starting material is controlled such that conversion of the $C_3$ chlorinated alkane starting material to the plurality of $C_3$ chlorinated alkane isomers, represented by the molar ratio of the $C_3$ chlorinated alkane starting material:$C_3$ chlorinated alkane isomers in the reaction mixture present in the chlorination zone, does not exceed about 40:60, wherein the process further comprises one or more distillation steps on the reaction mixture, said one or more distillation steps being carried out using distillation apparatus in direct communication with the chlorination zone and/or being carried out on reaction mixture extracted from the chlorination zone using distillation apparatus remote from the chlorination zone, and wherein the process further comprises the steps of feeding a mixture into an aqueous treatment zone, contacting the mixture with an aqueous medium and extracting a treated mixture comprising reduced levels of oxygenated compounds, wherein the mixture is a reaction mixture extracted from the chlorination zone, a plurality of $C_3$ chlorinated alkane isomer stream obtained via distillation from the reaction mixture or a partially distilled reaction mixture, wherein the partially distilled reaction mixture is a reaction mixture extracted from the chlorination zone from which one or more of an unreacted $C_3$ chlorinated alkane starting material stream, one or more single isomer streams and/or one or more distillation residue streams has already been obtained via distillation.

4. The process of claim 3, wherein the treated mixture comprises oxygenated organic compounds in amounts of about 1000 ppm or less.

5. The process of claim 3, wherein the aqueous treatment step precedes none, one, some or all of the distillation step/s.

6. A process for producing a reaction mixture comprising a plurality of $C_3$ chlorinated alkane isomers comprising chlorinating a $C_3$ chlorinated alkane starting material in a chlorination zone to produce the plurality of $C_3$ chlorinated alkane isomers, the plurality of $C_3$ chlorinated alkane isomers each having at least one more chlorine atom than the $C_3$ chlorinated alkane starting material, wherein the concentration of the $C_3$ chlorinated alkane starting material is controlled such that conversion of the $C_3$ chlorinated alkane starting material to the plurality of $C_3$ chlorinated alkane isomers, represented by the molar ratio of the $C_3$ chlorinated alkane starting material:$C_3$ chlorinated alkane isomers in the reaction mixture present in the chlorination zone, does not exceed about 40:60, wherein the process further comprises one or more distillation steps on the reaction mixture, said one or more distillation steps being carried out using distillation apparatus in direct communication with the chlorination zone and/or being carried out on reaction mixture extracted from the chlorination zone using distillation apparatus remote from the chlorination zone, and wherein the chlorination zone is conducted in a falling film tubular photoreactor and the molar ratio of the $C_3$ chlorinated alkane starting material:$C_3$ chlorinated alkane isomers in the reaction mixture does not exceed about 40:60.

* * * * *